(12) United States Patent
Dostmann et al.

(10) Patent No.: US 9,260,486 B2
(45) Date of Patent: Feb. 16, 2016

(54) PEPTIDIC ACTIVATORS OF TYPE I CGMP DEPENDENT PROTEIN KINASES AND USES THEREOF

(71) Applicants: Wolfgang Dostmann, Shelburne, VT (US); Brent W. Osborne, Ridgefield, NJ (US); Thomas M. Moon, Burlington, VT (US)

(72) Inventors: Wolfgang Dostmann, Shelburne, VT (US); Brent W. Osborne, Ridgefield, NJ (US); Thomas M. Moon, Burlington, VT (US)

(73) Assignee: The University of Vermont and State Agricultural College, Burlington, VT (US)

(*) Notice: Subject to any disclaimer, the term of this patent is extended or adjusted under 35 U.S.C. 154(b) by 0 days.

(21) Appl. No.: 13/801,235

(22) Filed: Mar. 13, 2013

(65) Prior Publication Data

US 2014/0037547 A1   Feb. 6, 2014

Related U.S. Application Data

(60) Provisional application No. 61/610,325, filed on Mar. 13, 2012.

(51) Int. Cl.

| | |
|---|---|
| *A61K 38/08* | (2006.01) |
| *A61K 38/10* | (2006.01) |
| *A61K 38/16* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/04* | (2006.01) |
| *C07K 1/00* | (2006.01) |
| *C07K 14/00* | (2006.01) |
| *A61K 45/00* | (2006.01) |
| *C12Q 1/48* | (2006.01) |
| *G06F 19/16* | (2011.01) |
| *A61K 45/06* | (2006.01) |
| *C07K 7/06* | (2006.01) |
| *C07K 7/08* | (2006.01) |

(52) U.S. Cl.
CPC ............ *C07K 14/00* (2013.01); *A61K 38/00* (2013.01); *A61K 38/08* (2013.01); *A61K 38/10* (2013.01); *A61K 38/16* (2013.01); *A61K 45/00* (2013.01); *A61K 45/06* (2013.01); *C07K 7/06* (2013.01); *C07K 7/08* (2013.01); *C07K 14/001* (2013.01); *C12Q 1/485* (2013.01); *G06F 19/16* (2013.01)

(58) Field of Classification Search
None
See application file for complete search history.

(56) References Cited

U.S. PATENT DOCUMENTS

2011/0012894 A1   1/2011   Wiesmann et al.
2012/0328653 A1*  12/2012  Pantaleo et al. ............ 424/206.1

OTHER PUBLICATIONS

Margaill et al., "Antioxidant strategies in the treatment of stroke," Free Radical Biology & Medicine 39:429-443 (2005).*
Neo et al., "Roles for redox mechanisms controlling protein kinase G in pulmonary and coronary artery responses to hypoxia," Am. J. Physiol. Circ. Physiol. 301:H2295-H2304 (First available Sep. 16, 2011).*
Oxford University, "Safety (MSDS) data for hydrogen peroxide, 3% aqueous solution", available online at https://www.lewisu.edu/academics/biology/pdf/Hydrogen_Peroxide-3.pdf, (2004).*
Wernet et al., "The cDNA of the two isoforms cGMP-dependent protein kinase," FEBS Lett. 251:191-196 (1989).*
Alverdi et al., cGMP-binding prepares PKG for substrate binding by disclosing the C-terminal domain. J Mol Biol. Feb. 1, 2008;375(5):1380-93. Epub Nov. 22, 2007.
Batchelor et al., Exquisite sensitivity to subsecond, picomolar nitric oxide transients conferred on cells by guanylyl cyclase-coupled receptors. Proc Natl Acad Sci U S A. Dec. 21, 2010;107(51):22060-5. doi: 10.1073/pnas.1013147107. Epub Dec. 6, 2010.
Berman et al., The cAMP binding domain: an ancient signaling module. Proc Natl Acad Sci U S A. Jan. 4, 2005;102(1):45-50. Epub Dec. 23, 2004.
Bian et al., Nitric oxide signaling in vascular biology. J Am Soc Hypertens. Jan.-Feb. 2007;1(1):17-29. doi: 10.1016/j.jash.2006.11.007.
Boettcher et al., Realizing the allosteric potential of the tetrameric protein kinase A RIα holoenzyme. Structure. Feb. 9, 2011;19(2):265-76. doi: 10.1016/j.str.2010.12.005.
Burgoyne et al., Cysteine redox sensor in PKGIa enables oxidant-induced activation. Science. Sep. 7, 2007;317(5843):1393-7. Epub Aug. 23, 2007.
Butt et al , Inhibition of cyclic GMP-dependent protein kinase-mediated effects by (Rp)-8-bromo-PET-cyclic GMPS. Br J Pharmacol. Dec. 1995;116(8):3110-6.
Caldwell et al., Direct modulation of the protein kinase A catalytic subunit α by growth factor receptor tyrosine kinases. J Cell Biochem. Jan. 2012;113(1):39-48. doi: 10.1002/jcb.23325.
Collaborative Computational Project, No. 4. The CCP4 suite: programs for protein crystallography. Acta Crystallogr D Biol Crystallogr. Sep. 1, 1994;50(Pt 5):760-3.
Das et al., cAMP activation of PKA defines an ancient signaling mechanism. Proc Natl Acad Sci USA. Jan. 2, 2007;104(1):93-8. Epub Dec. 20, 2006.
De La Fortelle et al., SHARP: A Maximum-Likelihood Heavy-Atom Parameter Refinement Program for the MIR and MAD Methods. Methods Enzymol. 1997;276:472-94.
Diller et al., Molecular basis for regulatory subunit diversity in cAMP-dependent protein kinase: crystal structure of the type II beta regulatory subunit. Structure. Jan. 10, 2001;9(1):73-82.

(Continued)

*Primary Examiner* — James H Alstrum Acevedo
*Assistant Examiner* — Thea D'Ambrosio
(74) *Attorney, Agent, or Firm* — Wolf, Greenfield & Sacks, P.C.

(57) ABSTRACT

The present invention relates to cGMP protein kinase (PKG) and regulatory domains and methods of use thereof. The structural determination of PKG domains is also described. cGMP independent PKG activators and uses thereof are also described.

6 Claims, 23 Drawing Sheets

(56) References Cited

OTHER PUBLICATIONS

Dostmann et al., Delineation of selective cyclic GMP-dependent protein kinase Ialpha substrate and inhibitor peptides based on combinatorial peptide libraries on paper. Pharmacol Ther. May-Jun. 1999;82(2-3):373-87.

Dostmann et al., The catalytic domain of the cGMP-dependent protein kinase Ialpha modulates the cGMP-binding characteristics of its regulatory domain. FEBS Lett. Dec. 2, 1996;398(2-3):206-10.

Dostmann, (RP)-cAMPS inhibits the cAMP-dependent protein kinase by blocking the cAMP-induced conformational transition. FEBS Lett. Nov. 20, 1995;375(3):231-4.

Dostmann et al., Identifying the molecular switches that determine whether (Rp)-cAMPS functions as an antagonist or an agonist in the activation of cAMP-dependent protein kinase I Biochemistry. Sep. 3, 1991;30(35):8710-6.

Dostmann et al., Probing the cyclic nucleotide binding sites of cAMP-dependent protein kinases I and II with analogs of adenosine 3',5'-cyclic phosphorothioates. J Biol Chem. Jun. 25, 1990;265(18):10484-91.

Green et al., Immunogenic structure of the influenza virus hemagglutinin. Cell. Mar. 1982;28(3):477-87.

Heil et al., A catalytically active fragment of cGMP-dependent protein kinase. Occupation of its cGMP-binding sites does not affect its phosphotransferase activity. Eur J Biochem. Oct. 1, 1987;168(1):117-21.

Hofmann et al., cGMP regulated protein kinases (cGK). Handb Exp Pharmacol. 2009;(191):137-62. doi: 10.1007/978-3-540-68964-5_8.

Kim et al., PKA-I holoenzyme structure reveals a mechanism for cAMP-dependent activation Cell. Sep. 21, 2007;130(6):1032-43.

Kornev et al., A generalized allosteric mechanism for cis-regulated cyclic nucleotide binding domains. PLoS Comput Biol. Apr. 11, 2008;4(4):e1000056. doi: 10.1371/journal.pcbi.1000056.

Kots et al., Nitric oxide and cyclic GMP signaling pathway as a focus for drug development. Curr Med Chem. 2011;18(22):3299-305.

Krissinel et al., Inference of macromolecular assemblies from crystalline state. J Mol Biol. Sep. 21, 2007;372(3):774-97. Epub May 13, 2007.

Kuhn, Molecular physiology of natriuretic peptide signalling. Basic Res Cardiol. Mar. 2004;99(2):76-82. Epub Jan. 23, 2004.

Landgraf et al., Oxidation of cysteines activates cGMP-dependent protein kinase. J Biol Chem. Sep. 5, 1991;266(25):16305-11.

Leonard et al., Crystal structure and allosteric activation of protein kinase C βII. Cell. Jan. 7, 2011;144(1):55-66. doi: 10.1016/j.cell.2010.12.013.

Nausch et al., Differential patterning of cGMP in vascular smooth muscle cells revealed by single GFP-linked biosensors. Proc Natl Acad Sci U S A. Jan. 8, 2008;105(1):365-70. doi: 10.1073/pnas.0710387105. Epub Dec. 28, 2007.

Nickl et al., (D)-Amino acid analogues of DT-2 as highly selective and superior inhibitors of cGMP-dependent protein kinase Ialpha. Biochim Biophys Acta. Mar. 2010;1804(3):524-32. doi: 10.1016/j.bbapap.2009.12.004. Epub Dec. 16, 2009.

Osborne et al., Crystal structure of cGMP-dependent protein kinase reveals novel site of interchain communication. Structure. Sep. 7, 2011;19(9):1317-27. doi: 10.1016/j.str.2011.06.012.

Palker et al., A conserved region at the COOH terminus of human immunodeficiency virus gp120 envelope protein contains an immunodominant epitope. Proc Natl Acad Sci USA. Apr. 1987;84(8):2479-83.

Pfeifer et al., Structure and function of cGMP-dependent protein kinases. Rev Physiol Biochem Pharmacol. 1999;135:105-49.

Pinkse et al., Mode of action of cGMP-dependent protein kinase-specific inhibitors probed by photoaffinity cross-linking mass spectrometry. J Biol Chem. Jun. 12, 2009;284(24):16354-68. doi: 10.1074/jbc.M808521200. Epub Apr. 15, 2009.

Rehmann et al., Capturing cyclic nucleotides in action: snapshots from crystallographic studies. Nat Rev Mol Cell Biol. Jan. 2007;8(1):63-73.

Scholten et al., The hinge region operates as a stability switch in cGMP-dependent protein kinase I alpha. FEBS J. May 2007;274(9):2274-86. Epub Apr. 2, 2007.

Steiner et al., cGMP-dependent protein kinase Ialpha associates with the antidepressant-sensitive serotonin transporter and dictates rapid modulation of serotonin uptake. Mol Brain. Aug. 5, 2009;2:26. doi: 10.1186/1756-6606-2-26.

Su et al., Regulatory subunit of protein kinase A: structure of deletion mutant with cAMP binding domains. Science. Aug. 11, 1995;269(5225):807-13.

Takio et al., Guanosine cyclic 3',5'-phosphate dependent protein kinase, a chimeric protein homologous with two separate protein families. Biochemistry. Aug. 28, 1984;23(18):4207-18.

Tegge et al., Determination of cyclic nucleotide-dependent protein kinase substrate specificity by the use of peptide libraries on cellulose paper. Biochemistry. Aug. 22, 1995;34(33):10569-77.

Wu et al., PKA type IIalpha holoenzyme reveals a combinatorial strategy for isoform diversity Science. Oct. 12, 2007;318(5848):274-9.

\* cited by examiner

```
                      PBC-A                              PBC-B
RIα        GEGGSFGELALIYGTPRAATVKA ... PSDYFGEIALLMNRPRAATVVA
RIβ        SEGGSFGELALIYGTPRAATVKA ... PSDYFGEIALLLNRPRAATVVA
RIIα       DNRGSFGELALMYNTPRAATIVA ... KGQYFGELALVTNKPRAASAYA
RIIβ       DNRGSFGELALMYNTPRAATITA ... RGQYFGELALVTNKPRAASAHA
PKG human  GPGKVFGELAILYNCTRTATVKT ... KGDWFGEKALQGEDVRTANVIA
PKG bovine GPGKVFGELAILYNCTRTATVKT ... KGDWFGEKALQGEDVRTANVIA
PKG pig    GPGKVFGELAILYNCTRTATVKT ... KGDWFGEKALQGEDVRTANVIA
PKG mouse  GPGKVFGELAILYNCTRTATVKT ... KGDWFGEKALQGEDVRTANVIA
PKG fish   GPGKVFGELAILYNCTRTATVRT ... RGDSFGEKALQGEDIRTANVIA
PKG fly    SGAKVLGELAILYNCQRTATITA ... KGDFFGEKALQGDDLRTANIIC
                              \Threonine       \Threonine
```

Fig. 7A

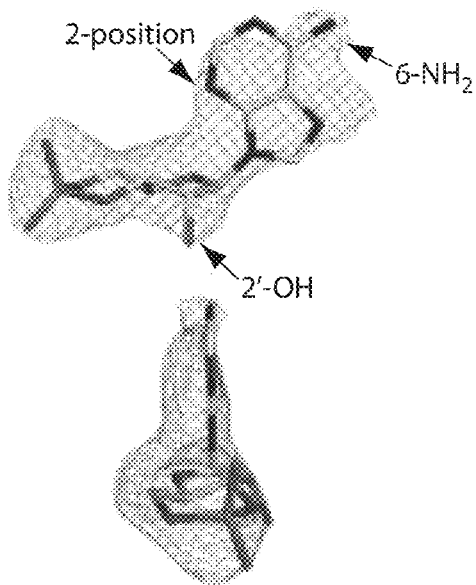

Fig. 7B

PKG-A : PKA-apo

PKG-A : PKA-cAMP

PKG-B : PKA-apo

PKG-B : PKA-cAMP

SEQUENCE LISTING

```
<160> NUMBER OF SEQ ID NOS: 45

<210> SEQ ID NO 1
<211> LENGTH: 279
<212> TYPE: PRT
<213> ORGANISM: Artificial Sequence
<220> FEATURE:
<223> OTHER INFORMATION: Synthetic Polypeptide
```

<400> SEQUENCE: 1

Gln Ala Phe Arg Lys Phe Thr Lys Ser Glu Arg Ser Lys Asp Leu Ile
1               5                   10                  15

Lys Glu Ala Ile Leu Asp Asn Asp Phe Met Lys Asn Leu Glu Leu Ser
            20                  25                  30

Gln Ile Gln Glu Ile Val Asp Cys Met Tyr Pro Val Glu Tyr Gly Lys
        35                  40                  45

Asp Ser Cys Ile Ile Lys Glu Gly Asp Val Gly Ser Leu Val Tyr Val
    50                  55                  60

Met Glu Asp Gly Lys Val Glu Val Thr Lys Glu Gly Val Lys Leu Cys
65                  70                  75                  80

Thr Met Gly Pro Gly Lys Val Phe Gly Glu Leu Ala Ile Leu Tyr Asn
                85                  90                  95

Cys Thr Arg Thr Ala Thr Val Lys Thr Leu Val Asn Val Lys Leu Trp
            100                 105                 110

Ala Ile Asp Arg Gln Cys Phe Gln Thr Ile Met Met Arg Thr Gly Leu
        115                 120                 125

Ile Lys His Thr Glu Tyr Met Glu Phe Leu Lys Ser Val Pro Thr Phe
    130                 135                 140

Gln Ser Leu Pro Glu Glu Ile Leu Ser Lys Leu Ala Asp Val Leu Glu
145                 150                 155                 160

Glu Thr His Tyr Glu Asn Gly Glu Tyr Ile Ile Arg Gln Gly Ala Arg
                165                 170                 175

Asp Gly Asp Thr Phe Phe Ile Ile Ser Lys Gly Lys Val Asn Val Thr
            180                 185                 190

Arg Glu Asp Ser Pro Asn Glu Asp Pro Val Phe Leu Arg Thr Leu Gly
        195                 200                 205

Lys Gly Asp Trp Phe Gly Glu Lys Ala Leu Gln Gly Glu Asp Val Arg
    210                 215                 220

Thr Ala Asn Val Ile Ala Ala Glu Ala Val Thr Cys Leu Val Ile Asp
225                 230                 235                 240

Arg Asp Ser Phe Lys His Leu Ile Gly Gly Leu Asp Asp Val Ser Asn
                245                 250                 255

Lys Ala Tyr Glu Asp Ala Glu Ala Lys Ala Lys Tyr Glu Ala Glu Ala
            260                 265                 270

Ala Phe Phe Ala Asn Leu Lys
        275

<210> SEQ ID NO 2
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 2

Asp Asp Val Ser Asn Lys Ala Tyr Glu Asp Ala Glu Ala Lys Ala Lys
1               5                   10                  15

Tyr Glu Ala Glu Ala Ala Phe Phe Ala Asn Leu Lys
            20                  25

<210> SEQ ID NO 3
<211> LENGTH: 12
<212> TYPE: PRT
<213> ORGANISM: Artificial Sequence
<220> FEATURE:

<223> OTHER INFORMATION: Synthetic Polypeptide

<400> SEQUENCE: 3

Thr Gln Ala Lys Arg Lys Lys Ser Leu Ala Met Ala
1               5                   10

<210> SEQ ID NO 4
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 4

Asp Val Ser Asn Lys Ala Tyr Glu Asp Ala Glu Ala Lys Ala Lys Tyr
1               5                   10                  15

Glu Ala Glu Ala Ala Phe Phe Ala Asn Leu Lys Leu Ser Asp
            20                  25                  30

<210> SEQ ID NO 5
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 5

Asp Val Ser Asn Lys Ala Tyr Glu Asp Ala Glu Ala Lys Ala Lys Tyr
1               5                   10                  15

Glu Ala Glu Ala Ala Phe Phe Ala Asn Leu Lys
            20                  25

<210> SEQ ID NO 6
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 6

Asp Val Ser Asn Lys Ala Tyr Glu Asp Ala Glu Ala Lys Ala Lys Tyr
1               5                   10                  15

Glu Ala Glu Ala Ala Phe Phe
            20

<210> SEQ ID NO 7
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 7

Ala Ala Phe Phe Ala Asn Leu Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is A, G, L, I, V, C, S, T or P

```
<220> FEATURE:
<221> NAME/KEY: misc_feature
<222> LOCATION: (2)..(2)
<223> OTHER INFORMATION: Xaa is A, G, L, I, V, C, S, T or P
<220> FEATURE:
<221> NAME/KEY: misc_feature
<222> LOCATION: (3)..(3)
<223> OTHER INFORMATION: Xaa is F, Y or W
<220> FEATURE:
<221> NAME/KEY: misc_feature
<222> LOCATION: (4)..(4)
<223> OTHER INFORMATION: Xaa is F, Y or W
<220> FEATURE:
<221> NAME/KEY: misc_feature
<222> LOCATION: (5)..(5)
<223> OTHER INFORMATION: Xaa is A, G, L, I, V, C, S, T or P
<220> FEATURE:
<221> NAME/KEY: misc_feature
<222> LOCATION: (6)..(6)
<223> OTHER INFORMATION: Xaa is N, D E, Q, S or T
<220> FEATURE:
<221> NAME/KEY: misc_feature
<222> LOCATION: (7)..(7)
<223> OTHER INFORMATION: Xaa is L, I, V or A
<220> FEATURE:
<221> NAME/KEY: misc_feature
<222> LOCATION: (8)..(8)
<223> OTHER INFORMATION: Xaa is K, R, E, H, D, Q, S, T or Y

<400> SEQUENCE: 8

Xaa Xaa Xaa Xaa Xaa Xaa Xaa Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 9

Phe Phe Ala Asn Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(2)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid

<400> SEQUENCE: 10

Xaa Xaa Phe Phe Ala Asn Leu Xaa
1               5

<210> SEQ ID NO 11
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 11

Gly Glu Gly Gly Ser Phe Gly Glu Leu Ala Leu Ile Tyr Gly Thr Pro
```

```
                1               5                   10                  15
Arg Ala Ala Thr Val Lys Ala
            20

<210> SEQ ID NO 12
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 12

Pro Ser Asp Tyr Phe Gly Glu Ile Ala Leu Ile Met Asn Arg Pro Arg
1               5                   10                  15

Ala Ala Thr Val Val Ala
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 13

Ser Glu Gly Gly Ser Phe Gly Glu Leu Ala Leu Ile Tyr Gly Thr Pro
1               5                   10                  15

Arg Ala Ala Thr Val Lys Ala
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 14

Pro Ser Asp Tyr Phe Gly Glu Ile Ala Leu Leu Leu Asn Arg Pro Arg
1               5                   10                  15

Ala Ala Thr Val Val Ala
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 15

Asp Asn Arg Gly Ser Phe Gly Glu Leu Ala Leu Met Tyr Asn Thr Pro
1               5                   10                  15

Arg Ala Ala Thr Ile Val Ala
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 16
```

```
Lys Gly Gln Tyr Phe Gly Glu Leu Ala Leu Val Thr Asn Lys Pro Arg
1               5                   10                  15

Ala Ala Ser Ala Tyr Ala
            20
```

<210> SEQ ID NO 17
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 17

```
Asp Asn Arg Gly Ser Phe Gly Glu Leu Ala Leu Met Tyr Asn Thr Pro
1               5                   10                  15

Arg Ala Ala Thr Ile Thr Ala
            20
```

<210> SEQ ID NO 18
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 18

```
Arg Gly Gln Tyr Phe Gly Glu Leu Ala Leu Val Thr Asn Lys Pro Arg
1               5                   10                  15

Ala Ala Ser Ala His Ala
            20
```

<210> SEQ ID NO 19
<211> LENGTH: 23
<212> TYPE: PRT
<213> ORGANISM: Homo sapiens

<400> SEQUENCE: 19

```
Gly Pro Gly Lys Val Phe Gly Glu Leu Ala Ile Leu Tyr Asn Cys Thr
1               5                   10                  15

Arg Thr Ala Thr Val Lys Thr
            20
```

<210> SEQ ID NO 20
<211> LENGTH: 22
<212> TYPE: PRT
<213> ORGANISM: Homo sapiens

<400> SEQUENCE: 20

```
Lys Gly Asp Trp Phe Gly Glu Lys Ala Leu Gln Gly Glu Asp Val Arg
1               5                   10                  15

Thr Ala Asn Val Ile Ala
            20
```

<210> SEQ ID NO 21
<211> LENGTH: 23
<212> TYPE: PRT
<213> ORGANISM: Bos taurus

<400> SEQUENCE: 21

```
Gly Pro Gly Lys Val Phe Gly Glu Leu Ala Ile Leu Tyr Asn Cys Thr
1               5                   10                  15

Arg Thr Ala Thr Val Lys Thr
            20
```

<210> SEQ ID NO 22
<211> LENGTH: 22
<212> TYPE: PRT
<213> ORGANISM: Bos taurus

<400> SEQUENCE: 22

Lys Gly Asp Trp Phe Gly Glu Lys Ala Leu Gln Gly Glu Asp Val Arg
1               5                   10                  15

Thr Ala Asn Val Ile Ala
            20

<210> SEQ ID NO 23
<211> LENGTH: 23
<212> TYPE: PRT
<213> ORGANISM: Sus scrofa

<400> SEQUENCE: 23

Gly Pro Gly Lys Val Phe Gly Glu Leu Ala Ile Leu Tyr Asn Cys Thr
1               5                   10                  15

Arg Thr Ala Thr Val Lys Thr
            20

<210> SEQ ID NO 24
<211> LENGTH: 22
<212> TYPE: PRT
<213> ORGANISM: Sus scrofa

<400> SEQUENCE: 24

Lys Gly Asp Trp Phe Gly Glu Lys Ala Leu Gln Gly Glu Asp Val Arg
1               5                   10                  15

Thr Ala Asn Val Ile Ala
            20

<210> SEQ ID NO 25
<211> LENGTH: 23
<212> TYPE: PRT
<213> ORGANISM: Mus musculus

<400> SEQUENCE: 25

Gly Pro Gly Lys Val Phe Gly Glu Leu Ala Ile Leu Tyr Asn Cys Thr
1               5                   10                  15

Arg Thr Ala Thr Val Lys Thr
            20

<210> SEQ ID NO 26
<211> LENGTH: 22
<212> TYPE: PRT
<213> ORGANISM: Mus musculus

<400> SEQUENCE: 26

Lys Gly Asp Trp Phe Gly Glu Lys Ala Leu Gln Gly Glu Asp Val Arg
1               5                   10                  15

Thr Ala Asn Val Ile Ala
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic Polypeptide

```
<400> SEQUENCE: 27

Gly Pro Gly Lys Val Phe Gly Glu Leu Ala Ile Leu Tyr Asn Cys Thr
1               5                   10                  15

Arg Thr Ala Thr Val Arg Thr
            20

<210> SEQ ID NO 28
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 28

Arg Gly Asp Ser Phe Gly Glu Lys Ala Leu Gln Gly Glu Asp Ile Arg
1               5                   10                  15

Thr Ala Asn Val Ile Ala
            20

<210> SEQ ID NO 29
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 29

Ser Gly Ala Lys Val Leu Gly Glu Leu Ala Ile Leu Tyr Asn Cys Gln
1               5                   10                  15

Arg Thr Ala Thr Ile Thr Ala
            20

<210> SEQ ID NO 30
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 30

Lys Gly Asp Phe Phe Gly Glu Lys Ala Leu Gln Gly Asp Asp Leu Arg
1               5                   10                  15

Thr Ala Asn Ile Ile Cys
            20

<210> SEQ ID NO 31
<211> LENGTH: 77
<212> TYPE: PRT
<213> ORGANISM: Artificial Sequence
<220> FEATURE:
<223> OTHER INFORMATION: Synthetic Polypeptide

<400> SEQUENCE: 31

Gln Ala Phe Arg Lys Phe Thr Lys Ser Glu Arg Ser Lys Asp Leu Ile
1               5                   10                  15

Lys Glu Ala Ile Leu Asp Asn Asp Phe Met Lys Asn Leu Glu Leu Ser
            20                  25                  30

Gln Ile Gln Glu Ile Val Asp Cys Met Tyr Pro Val Glu Tyr Gly Lys
        35                  40                  45

Asp Ser Cys Ile Ile Lys Glu Gly Asp Val Gly Ser Leu Val Tyr Val
    50                  55                  60

Met Glu Asp Gly Lys Val Glu Val Thr Lys Glu Gly Val
```

65                  70                  75

<210> SEQ ID NO 32
<211> LENGTH: 77
<212> TYPE: PRT
<213> ORGANISM: Artificial Sequence
<220> FEATURE:
<223> OTHER INFORMATION: Synthetic Polypeptide

<400> SEQUENCE: 32

Val Thr Leu Pro Phe Tyr Pro Lys Ser Pro Gln Ser Lys Asp Leu Ile
1               5                   10                  15

Lys Glu Ala Ile Leu Asp Asn Asp Phe Met Lys Asn Leu Glu Leu Ser
            20                  25                  30

Gln Ile Gln Glu Ile Val Asp Cys Met Tyr Pro Val Glu Tyr Gly Lys
        35                  40                  45

Asp Ser Cys Ile Ile Lys Glu Gly Asp Val Gly Ser Leu Val Tyr Val
    50                  55                  60

Met Glu Asp Gly Lys Val Glu Val Thr Lys Glu Gly Val
65                  70                  75

<210> SEQ ID NO 33
<211> LENGTH: 79
<212> TYPE: PRT
<213> ORGANISM: Artificial Sequence
<220> FEATURE:
<223> OTHER INFORMATION: Synthetic Polypeptide

<400> SEQUENCE: 33

Phe Ser Phe Glu Lys Ala Arg Val Arg Lys Asp Ser Ser Glu Lys Lys
1               5                   10                  15

Leu Ile Thr Asp Ala Leu Asn Lys Asn Gln Phe Leu Lys Arg Leu Asp
            20                  25                  30

Pro Gln Gln Ile Lys Asp Met Val Glu Cys Met Tyr Gly Arg Asn Tyr
        35                  40                  45

Gln Gln Gly Ser Tyr Val Ile Lys Gln Gly Glu Pro Gly Asn His Ile
    50                  55                  60

Phe Val Leu Ala Glu Gly Arg Leu Glu Val Phe Gln Gly Glu Lys
65                  70                  75

<210> SEQ ID NO 34
<211> LENGTH: 79
<212> TYPE: PRT
<213> ORGANISM: Artificial Sequence
<220> FEATURE:
<223> OTHER INFORMATION: Synthetic Polypeptide

<400> SEQUENCE: 34

Lys Leu Cys Thr Met Gly Pro Gly Lys Val Phe Gly Glu Leu Ala Ile
1               5                   10                  15

Leu Tyr Asn Cys Thr Arg Thr Ala Thr Val Lys Thr Leu Val Asn Val
            20                  25                  30

Lys Leu Trp Ala Ile Asp Arg Gln Cys Phe Gln Thr Ile Met Met Arg
        35                  40                  45

Thr Gly Leu Ile Lys His Thr Glu Tyr Met Glu Phe Leu Lys Ser Val
    50                  55                  60

Pro Thr Phe Gln Ser Leu Pro Glu Glu Ile Leu Ser Lys Leu Ala
65                  70                  75

<210> SEQ ID NO 35

```
<211> LENGTH: 79
<212> TYPE: PRT
<213> ORGANISM: Artificial Sequence
<220> FEATURE:
<223> OTHER INFORMATION: Synthetic Polypeptide

<400> SEQUENCE: 35

Leu Leu Ser Ser Ile Pro Met Trp Thr Thr Phe Gly Glu Leu Ala Ile
1               5                   10                  15

Leu Tyr Asn Cys Thr Arg Thr Ala Ser Val Lys Ala Ile Thr Asn Val
            20                  25                  30

Lys Thr Trp Ala Leu Asp Arg Glu Val Phe Gln Asn Ile Met Arg Arg
        35                  40                  45

Thr Ala Gln Ala Arg Asp Glu Glu Tyr Arg Asn Phe Leu Arg Ser Val
    50                  55                  60

Ser Leu Leu Lys Asn Leu Pro Glu Asp Lys Leu Thr Lys Ile Ile
65                  70                  75

<210> SEQ ID NO 36
<211> LENGTH: 77
<212> TYPE: PRT
<213> ORGANISM: Artificial Sequence
<220> FEATURE:
<223> OTHER INFORMATION: Synthetic Polypeptide

<400> SEQUENCE: 36

Asp Val Leu Glu Glu Thr His Tyr Glu Asn Gly Glu Tyr Ile Ile Arg
1               5                   10                  15

Gln Gly Ala Arg Asp Gly Asp Thr Phe Phe Ile Ile Ser Lys Gly Lys
            20                  25                  30

Val Asn Val Thr Arg Glu Asp Ser Pro Asn Glu Asp Pro Val Phe Leu
        35                  40                  45

Arg Thr Leu Gly Lys Gly Asp Trp Phe Gly Glu Lys Ala Leu Gln Gly
    50                  55                  60

Glu Asp Val Arg Thr Ala Asn Val Ile Ala Ala Glu Ala
65                  70                  75

<210> SEQ ID NO 37
<211> LENGTH: 76
<212> TYPE: PRT
<213> ORGANISM: Artificial Sequence
<220> FEATURE:
<223> OTHER INFORMATION: Synthetic Polypeptide

<400> SEQUENCE: 37

Asp Val Leu Glu Glu Thr His Tyr Glu Asn Gly Glu Tyr Ile Ile Arg
1               5                   10                  15

Gln Gly Ala Arg Gly Asp Thr Phe Phe Ile Ile Ser Lys Gly Lys Val
            20                  25                  30

Asn Val Thr Arg Glu Asp Ser Pro Asn Glu Asp Pro Val Phe Leu Arg
        35                  40                  45

Thr Leu Gly Lys Gly Asp Trp Phe Gly Glu Lys Ala Leu Gln Gly Glu
    50                  55                  60

Asp Val Arg Thr Ala Asn Val Ile Ala Ala Glu Ala
65                  70                  75

<210> SEQ ID NO 38
<211> LENGTH: 77
<212> TYPE: PRT
<213> ORGANISM: Artificial Sequence
<220> FEATURE:
```

<223> OTHER INFORMATION: Synthetic Polypeptide

<400> SEQUENCE: 38

Asp Cys Leu Glu Val Glu Tyr Tyr Asp Lys Gly Asp Tyr Ile Ile Arg
1               5                   10                  15

Glu Gly Glu Glu Gly Ser Thr Phe Phe Ile Leu Ala Lys Gly Lys Val
            20                  25                  30

Lys Val Thr Gln Ser Thr Glu Gly His Asp Gln Pro Gln Leu Ile Lys
        35                  40                  45

Thr Leu Gln Lys Gly Glu Tyr Phe Gly Glu Lys Ala Leu Ile Ser Asp
    50                  55                  60

Asp Val Arg Ser Ala Asn Ile Ile Ala Glu Glu Asn Asp
65                  70                  75

<210> SEQ ID NO 39
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 39

Val Thr Cys Leu Val Ile Asp Arg Asp Ser Phe Lys His Leu Ile Gly
1               5                   10                  15

Gly Leu Asp Asp Val Ser Asn Lys Ala Tyr Glu Asp Ala Glu Ala Lys
            20                  25                  30

Ala Lys Tyr Glu Ala Glu Ala Ala Phe Phe Ala Asn Leu Lys
        35                  40                  45

<210> SEQ ID NO 40
<211> LENGTH: 73
<212> TYPE: PRT
<213> ORGANISM: Artificial Sequence
<220> FEATURE:
<223> OTHER INFORMATION: Synthetic Polypeptide

<400> SEQUENCE: 40

Val Ala Cys Leu Val Ile Asp Arg Glu Thr Phe Asn Gln Thr Val Gly
1               5                   10                  15

Thr Phe Asp Glu Leu Gln Lys Tyr Leu Glu Gly Tyr Val Ala Thr Leu
            20                  25                  30

Asn Arg Asp Asp Glu Lys Arg His Ala Lys Arg Ser Met Ser Ser Trp
        35                  40                  45

Lys Leu Ser Lys Ala Leu Ser Leu Glu Met Ile Gln Leu Lys Glu Lys
    50                  55                  60

Val Ala Arg Phe Ser Ser Thr Ser Pro
65                  70

<210> SEQ ID NO 41
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 41

Asp Val Ser Asn Lys Ala Tyr Glu Asp Ala Glu Ala Lys Ala Lys Tyr
1               5                   10                  15

Glu Ala Glu Ala Ala Phe Phe
            20

```
<210> SEQ ID NO 42
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 42
cgggatccat gcaggcattc cggaagttc                                    29

<210> SEQ ID NO 43
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 43
ggaattccta ctacttcagg ttggcgaag                                    29

<210> SEQ ID NO 44
<211> LENGTH: 278
<212> TYPE: PRT
<213> ORGANISM: Artificial Sequence
<220> FEATURE:
<223> OTHER INFORMATION: Synthetic Polypeptide

<400> SEQUENCE: 44
```

Val Thr Leu Pro Phe Tyr Pro Lys Ser Pro Gln Ser Lys Asp Leu Ile
1               5                   10                  15

Lys Glu Ala Ile Leu Asp Asn Asp Phe Met Lys Asn Leu Glu Leu Ser
            20                  25                  30

Gln Ile Gln Glu Ile Val Asp Cys Met Tyr Pro Val Glu Tyr Gly Lys
        35                  40                  45

Asp Ser Cys Ile Ile Lys Glu Gly Asp Val Gly Ser Leu Val Tyr Val
    50                  55                  60

Met Glu Asp Gly Lys Val Glu Val Thr Lys Glu Gly Val Lys Leu Cys
65                  70                  75                  80

Thr Met Gly Pro Gly Lys Val Phe Gly Glu Leu Ala Ile Leu Tyr Asn
                85                  90                  95

Cys Thr Arg Thr Ala Thr Val Lys Thr Leu Val Asn Val Lys Leu Trp
            100                 105                 110

Ala Ile Asp Arg Gln Cys Phe Gln Thr Ile Met Met Arg Thr Gly Leu
        115                 120                 125

Ile Lys His Thr Glu Tyr Met Glu Phe Leu Lys Ser Val Pro Thr Phe
    130                 135                 140

Gln Ser Leu Pro Glu Glu Ile Leu Ser Lys Leu Ala Asp Val Leu Glu
145                 150                 155                 160

Glu Thr His Tyr Glu Asn Gly Glu Tyr Ile Ile Arg Gln Gly Ala Arg
                165                 170                 175

Gly Asp Thr Phe Phe Ile Ile Ser Lys Gly Lys Val Asn Val Thr Arg
            180                 185                 190

Glu Asp Ser Pro Asn Glu Asp Pro Val Phe Leu Arg Thr Leu Gly Lys
        195                 200                 205

Gly Asp Trp Phe Gly Glu Lys Ala Leu Gln Gly Glu Asp Val Arg Thr
    210                 215                 220

Ala Asn Val Ile Ala Ala Glu Ala Val Thr Cys Leu Val Ile Asp Arg
225                 230                 235                 240

Asp Ser Phe Lys His Leu Ile Gly Gly Leu Asp Asp Val Ser Asn Lys
                245                 250                 255

Ala Tyr Glu Asp Ala Glu Ala Lys Ala Lys Tyr Glu Ala Glu Ala Ala
            260                 265                 270

Phe Phe Ala Asn Leu Lys
        275

<210> SEQ ID NO 45
<211> LENGTH: 308
<212> TYPE: PRT
<213> ORGANISM: Artificial Sequence
<220> FEATURE:
<223> OTHER INFORMATION: Synthetic Polypeptide

<400> SEQUENCE: 45

Phe Ser Phe Glu Lys Ala Arg Val Arg Lys Asp Ser Ser Glu Lys Lys
1               5                   10                  15

Leu Ile Thr Asp Ala Leu Asn Lys Asn Gln Phe Leu Lys Arg Leu Asp
            20                  25                  30

Pro Gln Gln Ile Lys Asp Met Val Glu Cys Met Tyr Gly Arg Asn Tyr
        35                  40                  45

Gln Gln Gly Ser Tyr Val Ile Lys Gln Gly Glu Pro Gly Asn His Ile
    50                  55                  60

Phe Val Leu Ala Glu Gly Arg Leu Glu Val Phe Gln Gly Glu Lys Leu
65                  70                  75                  80

Leu Ser Ser Ile Pro Met Trp Thr Thr Phe Gly Glu Leu Ala Ile Leu
                85                  90                  95

Tyr Asn Cys Thr Arg Thr Ala Ser Val Lys Ala Ile Thr Asn Val Lys
            100                 105                 110

Thr Trp Ala Leu Asp Arg Glu Val Phe Gln Asn Ile Met Arg Arg Thr
        115                 120                 125

Ala Gln Ala Arg Asp Glu Glu Tyr Arg Asn Phe Leu Arg Ser Val Ser
    130                 135                 140

Leu Leu Lys Asn Leu Pro Glu Asp Lys Leu Thr Lys Ile Ile Asp Cys
145                 150                 155                 160

Leu Glu Val Glu Tyr Tyr Asp Lys Gly Asp Tyr Ile Ile Arg Glu Gly
                165                 170                 175

Glu Glu Gly Ser Thr Phe Phe Ile Leu Ala Lys Gly Lys Val Lys Val
            180                 185                 190

Thr Gln Ser Thr Glu Gly His Asp Gln Pro Gln Leu Ile Lys Thr Leu
        195                 200                 205

Gln Lys Gly Glu Tyr Phe Gly Glu Lys Ala Leu Ile Ser Asp Asp Val
    210                 215                 220

Arg Ser Ala Asn Ile Ile Ala Glu Glu Asn Asp Val Ala Cys Leu Val
225                 230                 235                 240

Ile Asp Arg Glu Thr Phe Asn Gln Thr Val Gly Thr Phe Asp Glu Leu
                245                 250                 255

Gln Lys Tyr Leu Glu Gly Tyr Val Ala Thr Leu Asn Arg Asp Asp Glu
            260                 265                 270

Lys Arg His Ala Lys Arg Ser Met Ser Ser Trp Lys Leu Ser Lys Ala
        275                 280                 285

Leu Ser Leu Glu Met Ile Gln Leu Lys Glu Lys Val Ala Arg Phe Ser
    290                 295                 300

Ser Thr Ser Pro
305

PEPTIDIC ACTIVATORS OF TYPE I CGMP DEPENDENT PROTEIN KINASES AND USES THEREOF

RELATED APPLICATIONS

This application claims priority under 35 U.S.C. §119(e) to U.S. Provisional Application Ser. No. 61/610,325, entitled "cGMP DEPENDENT PROTEIN KINASE," filed on Mar. 13, 2012, which is herein incorporated by reference in its entirety.

FEDERALLY SPONSORED RESEARCH

This invention was made with Government support under NIH grant number HL068891. Accordingly, the Government has certain rights in this invention.

FIELD OF THE INVENTION

The present invention relates to activators of type I isoforms of cGMP dependent protein kinase (PKG) and methods of use and synthesis thereof. Methods for expression and structural determination of regulatory domains of PKG are also described.

BACKGROUND OF THE INVENTION

PKG serves as an integral component of second messenger signaling. In smooth muscle, the PKG isoforms Iα and Iβ integrate the nitric oxide (NO) and natriuretic peptide-mediated signal transduction pathways by modulating intracellular $Ca^{2+}$, cell contractility, and—ultimately—blood flow (Hofmann et al., 2009; Francis et al., 1999; Pfeifer et al., 1999). Understanding the regulatory mechanism of the PKG holoenzyme is central to guiding pharmacological discoveries relevant to prevention and treatment of vascular diseases. Direct pharmaceutical targeting of PKG Iα however, has remained unsuccessful, largely due to the enzyme's complex, multi-domain architecture.

SUMMARY OF THE INVENTION

The present invention relates to PKG, regulatory domains of PKG, methods of use and synthesis thereof, and therapeutic and diagnostic reagents for modulating PKG. To better understand the molecular details of PKG regulation, we solved the first crystal structure of the intact regulatory domain of PKG Iα: 78-355 (PDBID: 3SHR). This structure exposed a unique helical domain, that we termed the Switch helix (SW). The SW stabilizes an unexpected dimer interface between protomers called the 'knob/nest'. The SW locus is important for maintaining the structural integrity of PHG Iα and serves as a key domain in PKG holoenzyme function and acts as a modulator of the molecular forces that govern PHG Iα activation.

The structure of the PKG regulatory domain identified according to the invention challenges the classic parallel-dimer view of PKG holoenzyme assembly (FIG. 1). The novel SW interface offers a dynamic view of trans-asymmetric protomers and its function in the activation of PKG. The isoform-specific interprotomer coupling of PKG is mediated by SW and is required for native kinase activity. We identified a set of residues within the switch helix, termed the 'knob' that specifically interacts with a hydrophobic 'nest' mainly provided by the cGMP B-site. The knob/nest interaction is allosterically linked to the cGMP B-site and provides the structural basis for cooperativity in PKG isoforms. The invention includes compounds which competitively and allosterically activate PKG and modulate vasodilation in vascular smooth muscle. The use of these compounds, referred to herein as cGMP independent PKG activators as competitive disruptors of the regulatory/catalytic domain interaction provides a significant advance in a number of therapeutic areas. The compounds are an entirely new class of PKG activators.

In some aspects the invention is a method for activating PKG, by contacting a cell with a cGMP independent PKG activator in an effective amount to activate PKG in the cell.

In other aspects the invention is a method of treating a PKG deficient condition in a subject, comprising administering to the subject a therapeutically effective amount of a cGMP independent PKG activator. The PKG deficient condition is selected from the group consisting of cardiovascular disorders, hypoxia, spinal cord injury, and stroke in some embodiments.

The subject may also be administered another compound in the methods of the invention. In some embodiments the other compound is cGMP. In other embodiments the other compound is a cGMP dependent PKG activator, such as a PDE inhibitor or a NO-donor. In some embodiments the PDE inhibitor is selected from the group consisting of sildenafil citrate, vinpocetine, EHNA, anagrelide, enoximone, milrinone, mesembrine, rolipram, ibudilast, piclamilast, luteolin, drotaverine, roflumilast, tadalafil, vardenafil, udenafil, avanafil, and papaverine. In other embodiments the NO-donor is selected from the group consisting of isosorbide dinitrite, Diazeniumdiolates, NONOates, S-Nitrosothiols, NO hybrid drugs, and Zeolites.

The cGMP independent PKG activator may be any type of molecule. In some embodiments it is a peptide, and optionally any of the peptides disclosed herein. An exemplary peptide of the invention is DVSNKAYEDAEAKAKYEAEAAFFANLKLSD (SEQ ID NO. 4). In other embodiments the cGMP independent PKG activator is a small molecule.

In other aspects the invention is a composition comprising: a cGMP independent PKG activator and a carrier. The cGMP independent PKG activator may be a peptide, such as DVSNKAYEDAEAKAKYEAEAAFFANLKLSD (SEQ ID NO. 4). Alternatively the cGMP independent PKG activator may be a small molecule.

A crystal comprising a regulatory domain of PKG is provided according to other aspects of the invention. The regulatory domain of PKG in the crystal comprises the amino acid sequence of SEQ ID NO: 1, wherein the crystal has unit cell dimensions of a=180.2 Angstroms, b=66.0 Angstroms, and c=81.6 Angstroms, with a unit cell variability of 5% in all dimensions. In some embodiments the PKG regulatory domain of the crystal has a three-dimensional structure comprising two cGMP binding domains, A and B, a hinge region and a switch helix domain.

A crystalline composition is provided in other aspects of the invention. The crystalline composition has a regulatory domain of PKG, wherein the PKG regulatory domain of the crystal has a three-dimensional structure comprising two cGMP binding domains, A and B, a hinge region and a switch helix domain.

The invention in other aspects is a regulatory domain of PKG in crystalline form comprising the amino acid sequence 78-355 and having the structural coordinates as deposited in Protein Data Bank with accession code 3SHR.

In yet other aspects, the invention is a crystallized PKG or portion thereof, wherein said crystallized PKG or portion thereof is crystallized under appropriate conditions such that the three dimensional structure of the PKG can be determined.

A method of selecting or designing a compound that interacts with PKG and modulates PKG activity is also provided according to aspects of the invention. The method comprises the step of assessing the stereochemical complementarity between the compound and a topographic region of PKG, wherein the topographic region of the PKG is characterized by at least a portion of the amino acids positioned at atomic coordinates as deposited in Protein Data Bank with accession code 3SHR wherein amino acid sequences of switch helix domain thereof are set forth as SEQ ID NO: 2. In some embodiments the topographic region of PKG is the switch helix domain defined by amino acids: 350-354. In other embodiments the method further involves testing the compound in vitro or in vivo for its capacity to modulate the activity of PKG.

In some aspects the invention is an isolated peptide comprising $X_1X_2X_3X_4X_5X_6X_7X_8$ (SEQ ID NO: 8), wherein each X is an amino acid, and wherein the peptide binds to a nest region or PKG. In some embodiments the Xs have the following values: $X_1$ is Ala, Gly, Leu, Ile, Val, Cys, Ser, Thr, or Pro; $X_2$ is Ala, Gly, Leu, Ile, Val, Cys, Ser, Thr, or Pro; $X_3$ is Phe, Tyr, or Trp; $X_4$ is Phe, Tyr, or Trp; $X_5$ is Ala, Gly, Leu, Ile, Val, Cys, Ser, Thr, or Pro; $X_6$ is Asn, Asp, Glu, Gln, Ser, or Thr; $X_7$ is Leu, Ile, Val, or Ala, and $X_8$ is Lys Arg, Glu, His, Asp, Gln, Ser, Thr, or Tyr.

In other embodiments the Xs have the following values: $X_1$ is Ala, Gly, Leu, Ile, or Val; $X_2$ is Ala, Gly, Leu, Ile, or Val; $X_3$ is Phe, Tyr, or Trp; $X_4$ is Phe, Tyr, or Trp; $X_5$ is Ala, Gly, Leu, Ile, or Val; $X_6$ is Asn, Asp, or Glu; $X_7$ is Leu, Ile, Val, or Ala, and $X_8$ is Lys or Arg.

In other embodiments the peptide comprises $X_1X_2$FFANL$X_8$ (SEQ ID NO: 10), such that $X_1X_2$, and $X_8$ are any amino acid, optionally Ala of Lys.

An isolated peptide comprising, consisting of or consisting essentially of FFANL (SEQ ID NO: 9) is provided according to other aspects of the invention.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DETAILED DESCRIPTION

Figure 1:
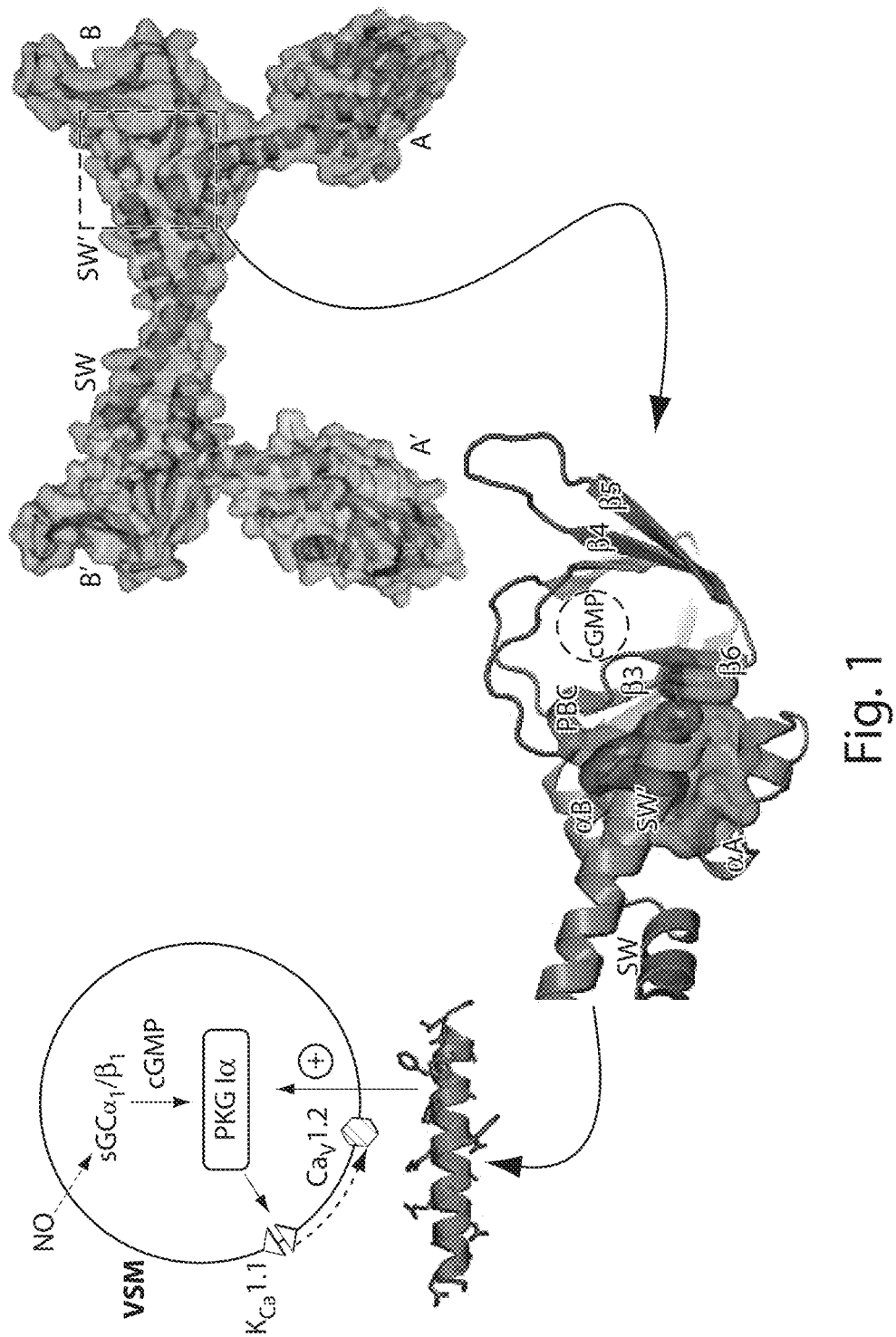
FIG. 1: Outline of the specific application for the activation of cGMP-dependent protein kinase given by the invention. Our new structure of PKG identified a hitherto unknown interaction between protomers (upper right). This interaction, called the knob/nest, is provided by the helical element (SW) and the formation of a hydrophobic pocket (nest) by the cGMP B-domain (bottom). A synthetic derivative of SW activates PKG in vitro and in vivo (upper left).

The cGMP-dependent protein kinase (PKG) serves as an integral component of second messenger signaling in a number of biological contexts including cell differentiation, memory, and vasodilation. PKG is homodimeric and large conformational changes accompany cGMP binding. However, the structure of PKG and the molecular mechanisms associated with protomer communication following cGMP-induced activation were unknown. According to the invention a 2.5 Å crystal structure of a regulatory domain construct (aa 78-355) containing both cGMP binding sites of PKGIα was developed. A distinct and segregated architecture with an extended central helix separates the two cGMP binding domains. Additionally, a previously uncharacterized helical domain (switch helix) promotes the formation of a hydrophobic interface between protomers. Mutational disruption of this interaction in full-length PKG implicates the switch helix as a critical site of dimer communication in PKG biology. These results offer new structural insight into the mechanism of allosteric PKG to activation. The coordinates of the structure have been deposited in the Protein Data Bank with accession code 3SHR and are hereby incorporated by reference in their entirety. The crystal structure of the invention is useful for elucidating the mechanisms of action of PKG as well as for identifying novel therapeutics that may be used for treating a variety of diseases.

The greatest structural distinction between the two major cyclic nucleotide regulated protein kinases, PKA and PKG, is the fact that PKG maintains both its regulatory and catalytic elements on the same polypeptide chain (Gill et al., 1977), while PKA is divided into subunits (Gill and Garren, 1971). To better understand how these molecular differences contribute to the unique characteristics of each kinase, we crystallized the central portion of the regulatory domain of PKG Iα. While prokaryotic expression of PKG constructs containing the catalytic domain yields inactive, misfolded protein that is sequestered to inclusion bodies (Feil et al., 1993), previous attempts to crystallize full-length PKG from mammalian systems have been unsuccessful as well. This is in part due to conformational heterogeneity stemming from mixed phosphorylation states at the N terminus and a proteolytically exposed hinge at Arg$^{77}$ (Aitken et al., 1984; Heil et al., 1987; Scholten et al., 2007). We identified according to the invention that exclusion of both the N-terminal D/D domain, as well as the C-terminal catalytic domain gave rise to a stable, monomeric fragment that is readily expressed in *Escherichia coli*. Multiple regulatory fragments were designed to encompass both tandem cGMP-binding domains (PKG$^{78-326}$, PKG$^{78-341}$ and PKG$^{78-355}$). The standard method for purification of recombinant PKG utilizes cyclic nucleotide affinity chromatography which saturates the allosteric binding sites through an elution with high concentrations of cNT (Dostmann et al., 1999). To prevent this artificial exposure of PKG protein to cNTs, PKG constructs were engineered with N-terminal hexa-histidine tags and purified using standard immobilized metal affinity chromatography (IMAC) methods. Three PKG regulatory domain constructs (PKG$^{78-326}$, PKG$^{78-341}$, and PKG$^{78-355}$) were prepared. Despite high yielding, stable expression of all three constructs, only PKG$^{78-355}$ yielded diffraction-quality crystals. The crystal structure is described below in detail in the Examples section.

PKG I serves as the main intracellular receptor for cGMP and is a key branch points of the nitric oxide (NO) and natriuretic peptide mediated signaling pathways. Most drugs, known to increase cGMP such as nitrates and inhibitors of phosphodiesterases, are mediating their effects through PKG (Bryan et al., 2009; Kots et al., 2011; Schlossmann et al., 2005). These kinases modulate learning and memory, renin release, intestinal secretion, platelet aggregation as well as vascular, gastrointestinal, bladder and penile smooth muscle relaxation (Kemp-Harper et al., 2009; Sandner et al., 2009; Walter et al., 2009; Kleppish et al., 2009). The structure of the PKG regulatory domain identified according to the invention, uncovered a unique, previously unrecognized helical domain (SW) that is important in kinase assembly and functionality. The presence of the SW directly contradicts prior models that focus solely on the N-terminus as the only site of dimerization.

Based on these findings we developed an alternative view of PKG holoenzyme activation, which helps resolve important unanswered questions regarding the role of dimerization in the cyclic-GMP dependent protein kinases, in particular; and, the role of symmetry in allosteric enzyme regulation, in general. The discovery of the SW and the location of its binding site has prompted the development of SW-derived PKG activators. These molecules have been shown to be functionally relevant by targeting PKG to elevate the open probability of large-conductance potassium channels ($K_{Ca}1.1$) in a similar fashion to that of cGMP. Therefore, SW-derivatives may provide a new platform for targeting the activity of PKG isoforms independent of the classic nitric oxide and natriuretic peptide driven pathways.

All our experimental protocols have employed refined expression techniques that allow us to control the exposure to cyclic nucleotides and the degree of auto-phosphorylation in our recombinant preparations of PHG Iα (deletion fragments and native enzyme). As a result, we solved the first crystal structure of any large fragment of PKG. This structure of PHG Iα (78-356) contains the majority of the regulatory domain and the novel SW domain, which forms an intermolecular boundary between the regulatory and the catalytic domains. The experimental conditions that lead to solving the structure have precipitated additional advances in obtaining crystals from other PKG constructs.

Figure 2:
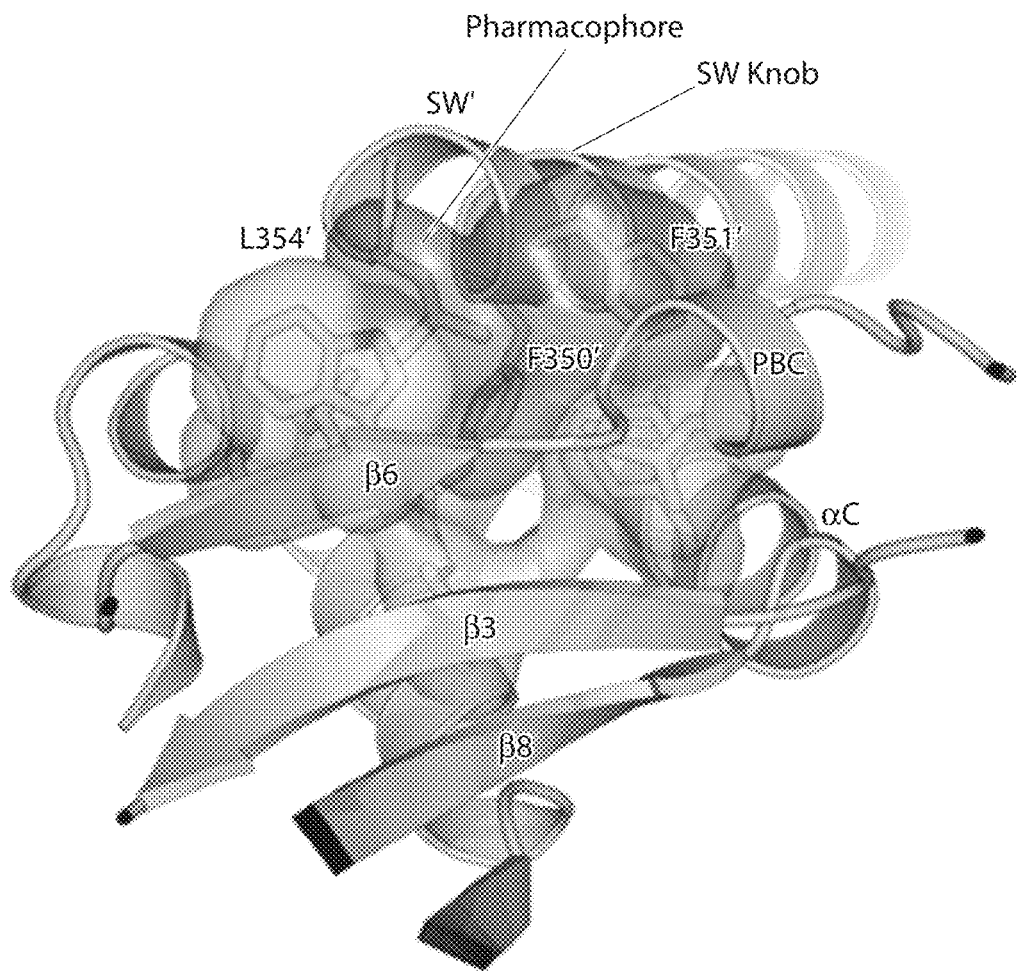
FIG. 2: A view of the pharmacophore derived from the SW knob forming specific interactions with the nest in the cGMP B-site.

This interchain communication between PKG protomers is surprisingly concise, showing the hallmarks of a drug/receptor architecture, which we termed knob/nest interaction (Shown in FIG. 2). Peptidic fragments of the SW domain not only bind competitively to native PKG Iα, but also activate the enzyme through an allosteric mechanism that involves the cGMP-binding site B. SW peptides present the first class of small non-cyclic nucleotide molecules capable of activating PKG.

Figure 11A:
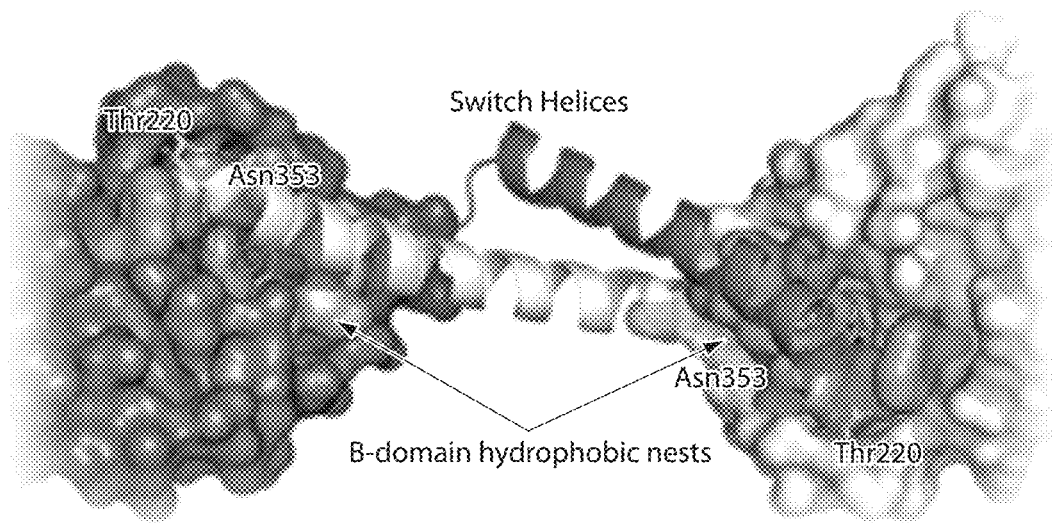
FIG. 11 Structural Details of the Switch Helix-Mediated Dimer Interface (A) "Top" view of switch helices (SW) and their assemblage with the neighboring B-domain: hydrophobic knobs at the end of the SW, residues that comprise a hydrophobic nest in the B-domain. (B) Details of the knob-nest assembly that mediates PKG$^{78-355}$ dimerization. The switch helix (lightest gray), and helical features from the neighboring B-domain (darkest gray) are represented as ribbons. (C) Kinetic Analysis of WT PKG Iα (●) and SW knob mutants F$^{350}$A, F$^{351}$A, L$^{354}$A (■), N$^{353}$A (◇), and F$^{350}$A, F$^{351}$A, N$^{353}$A, L$^{354}$A (◆).
Figure 11B:
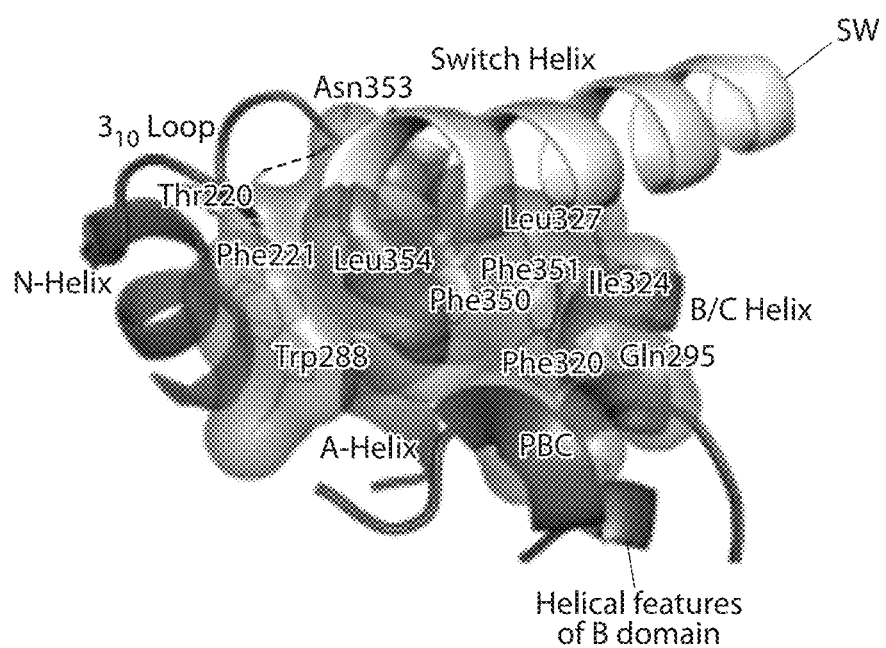

We also discovered that a shortened sequence containing only the knob residues is sufficient to activate PKG (SW:348-355 AAFFANLK, SEQ ID NO. 7). This confirms that the knob and its defined stereochemical orientation is the essential pharmacophore for this new target site within PKG necessary to activate PKG. As shown in FIG. 2, the pharmacophore is provided by the contiguous arrangement of Phe350, Phe351, and Leu354. This hydrophobic pocket provides approximately 20 kcal/mol of van der Waals interaction energy. In addition, the pharmacophore is supplemented by a hydrogen bond provided by Asn353 that lends specificity to the activator sequence (FIGS. 11A and 11B).

The maintenance and modulation of smooth muscle tone is a persistent topic of investigation due to the pervasive nature of cardiovascular disease in aging populations (Roger et al., 2011). The cGMP-dependent protein kinase lies at the heart of the regulation of smooth muscle and acts as the gatekeeper for nitric oxide and natriuretic peptide pathways (Kuhn, 2004; Bian et al., 2007; McDonald et al., 1995). Therefore, it comes as a surprise that the past thirty years have yielded little definitive information regarding the structure and function of this essential signaling node. The solution of the crystal structure of the largest fragment of PHG Iα has advanced the understanding of type I isoforms of PKG to include its reliance on the SW domain.

The knob/nest interactions display several critical features of a typical ligand/drug-receptor binding site. The surface area provided by the nest is stereo-chemically well-defined and suitable for accepting small organic molecules as supplied by the native knob residues FFANL (MW=610 Da) that are also sterochemically defined (FIG. 2). The van-der-Waals, dipole and H— bond interactions are woven into a concise network typically observed in drug-receptor sites. Further, the native affinity between knob and nest residues is driven by hydrophobic interactions (F350, F351, L354) that convey binding affinity as well as hydrogen-bond interactions (N353, T220) that are known to contribute to binding specificity (FIG. 2). The nest is accessible, yet sufficiently deep to fully engulf small ligands. These features prompted us to synthesize derivatives of the knob in an effort to ascertain if molecules capable of mimicking the knob/nest interaction could competitively displace the native SW domain and what consequences that would have on the function of PKG.

Figure 3A:
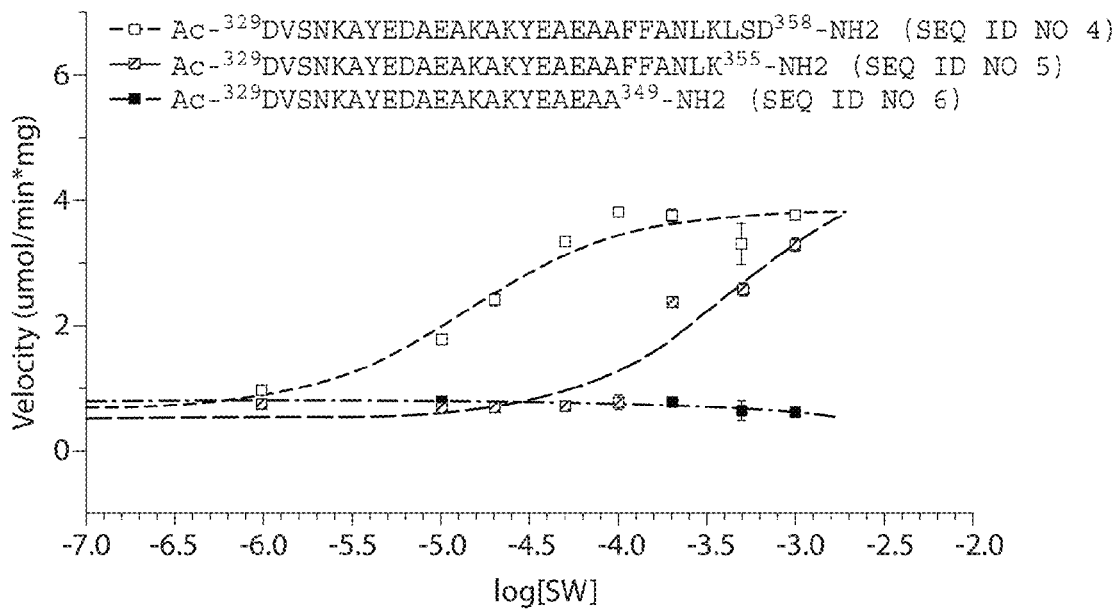
FIG. 3: A) Activation of PHG Iα is attenuated by varying the C-terminus of SW-derived peptides in the presence of 100 nM cGMP. Truncation of the knob residues abolishes peptide-based activation of PKG. B) A Schlid plot of the Rp-PET mediated inhibition of activation of PHG Iα by SW:329-358. INSET: Secondary analysis of the concentration-dependency of Rp-PET on the activation. Rp-PET appears to sterically inhibits closure of the PBC, thus attenuating the activation PKG by the SW.
Figure 3B:
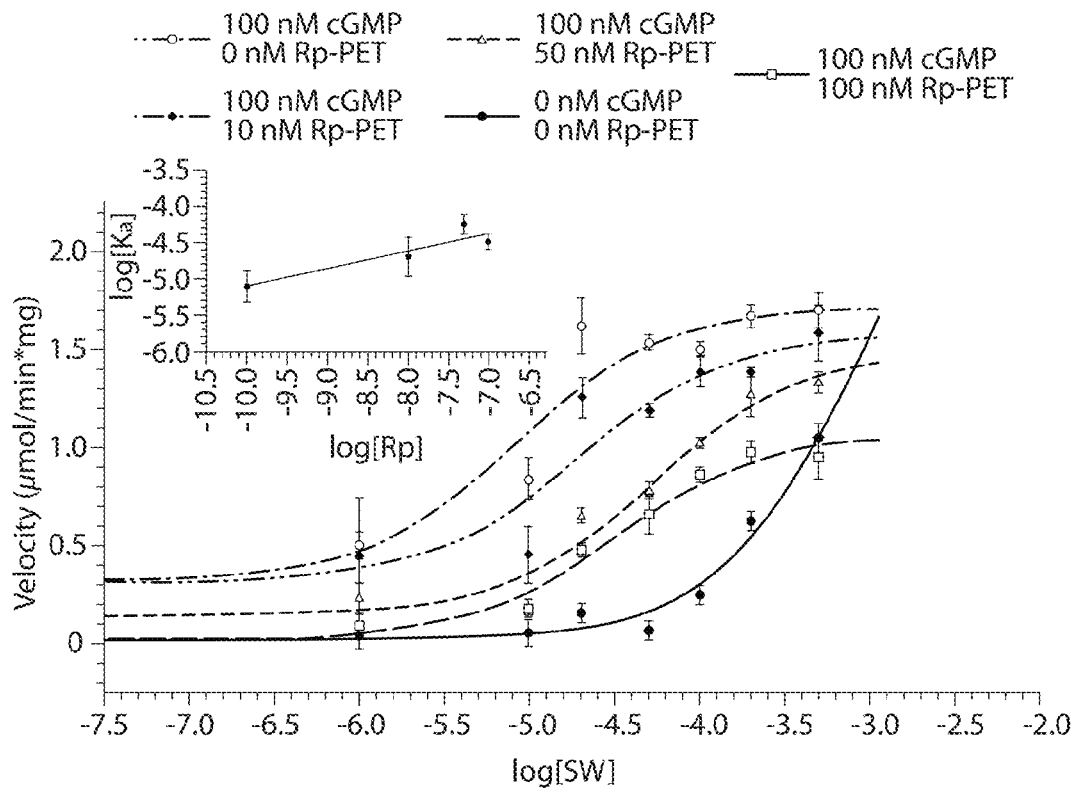

Starting with the 29-mer peptide (329-358), covering the full length of the switch helix, an array of peptide derivatives were synthesized to study the contributions from different segments of the SW helix peptide towards the functional phenotype of PKG Iα. Circular dichroism spectroscopy confirmed that the 29-mer SW peptide adopted a helical secondary structure. Reversible binding of SW:329-358 to wild-type PKG Ia was confirmed by surface-plasmon-resonance, while a sequence-scrambled control peptide demonstrated no binding. More importantly, SW: 329-358 dose-dependently activated PKG Ia (Ka=500 µM) as determined by 32P-incorporation assay (FIG. 3). The knob/nest interaction occurs at a site adjacent to the B-site that is associated with cGMP binding. Priming the kinase with 100 nM cGMP resulted in a 20-fold shift in the SW329-358 mediated activation profile of PKG Iα (Ka=40 µM), strongly reiterates the synergistic cross-talk between the cGMP-B site and the knob/nest. Under cGMP priming conditions, removal of the C-terminal residues LSD was sufficient to markedly decrease the peptides activation potential (SW:329-355 Ka=500 µM). Additional removal of the knob residues (SW:329-349) rendered a completely inactive SW-peptide derivative (FIG. 3). To further test if the knob is not only necessary but also sufficient to activate PKG, we synthesized an 8-mer peptide that consisted only of the minimal knob motif (SW:348-355 AAFFANLK, SEQ ID NO. 7). This knob-derived peptide did in fact activate PKG (Ka=500 µM) albeit weakly, corresponding to 30% of activation associated with cGMP. The activity of this short peptide is surprising. To activate the kinase, this non-helical 8-mer peptide first has to adopt the active helical conformation to activate PKG. However, this finding provides critical support in favor that the confined knob/nest interaction site may serve as a novel target site for non-cyclic nucleotide driven activation of PKG.

As outlined above, we have observed that SW:329-358 activates PHG Iα in vitro and acts synergistically with cGMP to modulate activation. The isolation of the SW independent from the kinase allows us to discretely probe the nest in future studies using native and non-native amino acids. Moreover, the use of the SW: 329-358 allows us to answer more fundamental questions about the nature of the regulatory and catalytic domains and the communication between the B-site and the nest. Cyclic nucleotide analogs have been used in previous investigations to competitively inhibit PKA and PKG (Dostmann et al., 1990; Dostmann and Taylor, 1991; Ogreid et al., 1994; Dostmann, 1995). In particular, (RP)-8-Br-PET-cGMPS (Rp-PET) is a commercially-available analog that has a higher affinity for the PHG Iα regulatory domain binding sites than cGMP (Butt et al., 1995). The structure of this inhibitor contains a β-phenyl-1,$N^2$-etheno group attached to the pyrimidine ring. We hypothesized previously, based upon structural observations, that the presence of this phenyl group in the syn orientation effectively blocks PBC closure and reduces the potency of the SW:329-358 in a dose-dependent manner. We have now found that when the Rp-PET is titrated into reactions measuring activation of PHG Iα by SW:329-358, we observed a linear response of the activation constant to the amount of Rp-PET titrated (FIG. 3). These results fully support our hypothesis that the knob is influenced by changes in the PBC, associated with the cGMP binding event.

Figure 4A:
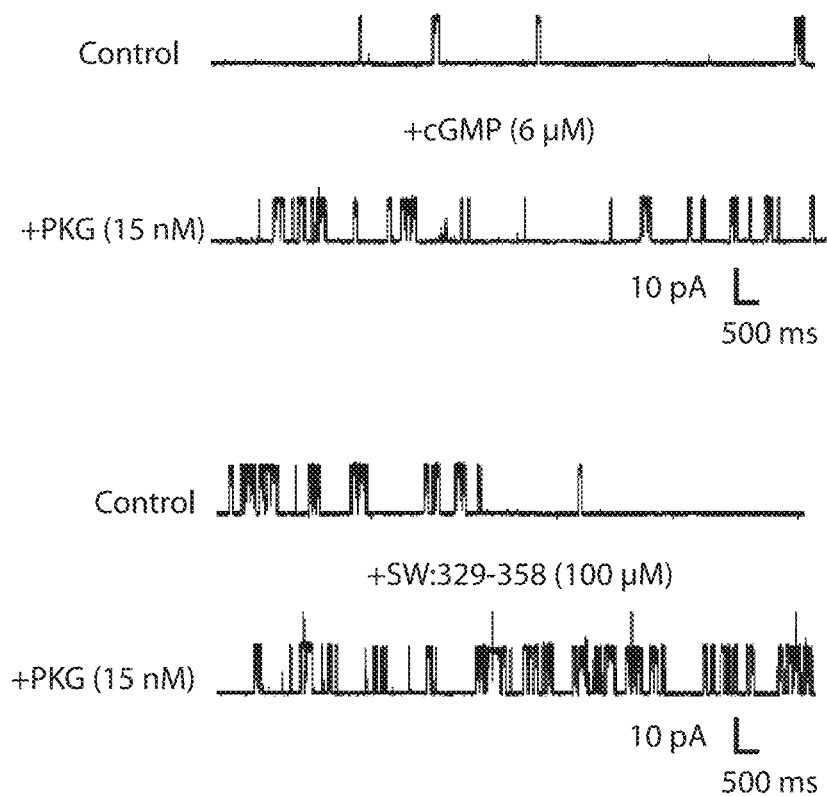
FIG. 4: SW:329-358 activates single $K_{Ca}$ channels in inside-out membrane patches excised from cerebral artery myocytes. A) Original records of single $K_{Ca}$ channels showing the activating effects of cGMP (left) and SW:329-358 (right) in the presence of PHG Ia and ATP. B) $K_{Ca}$ channel open-probability ($NP_O$) is significantly increased by cGMP or SW:329-358 vs. PKG alone. C) A sequence-scrambled derivative of SW:329-358 does not increase $K_{Ca}$ channel activity.
Figure 4B:
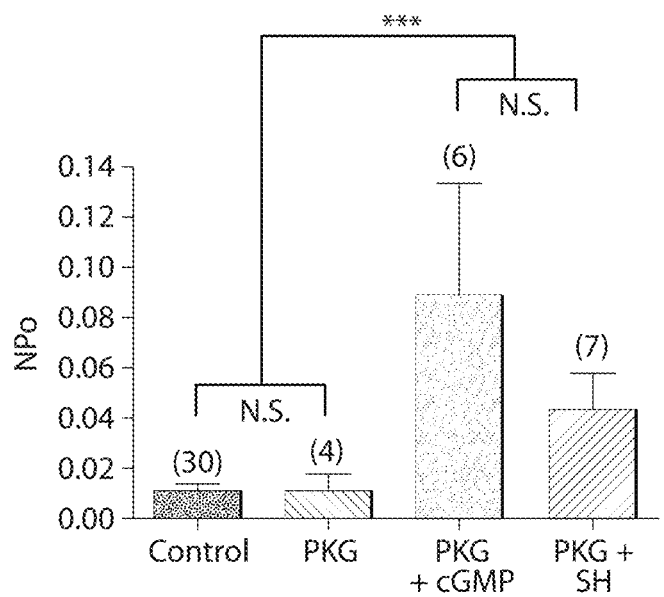
Figure 4C:
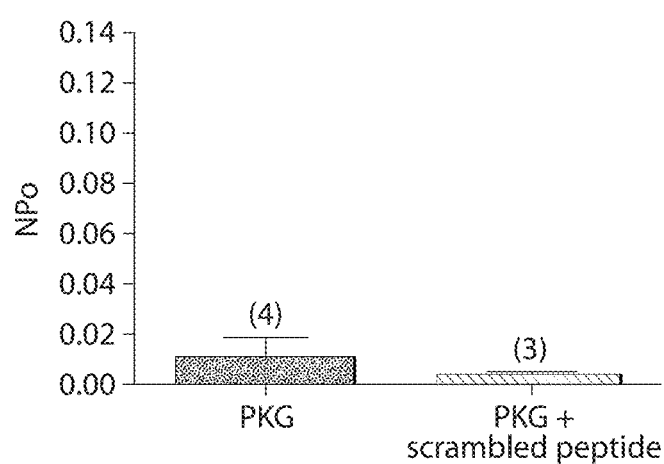

Once we had supporting evidence that molecules carrying the knob-type ligand conformation were capable of activating PKG we set out to determine if this novel mechanism of kinase activation was functionally relevant. The high conductance calcium-activated potassium channel $K_{Ca}1.1$ is a well-established intracellular target of PHG Iα in vascular smooth muscle (VSM) cells. Using inside-out patch clamp configurations from freshly dissociated VSM cells from rat posterior cerebral arteries, we measured the changes of open probability ($NP_O$) of single KCa1.1 channels in response to PKG stimulation in membrane patches excised from freshly-dissociated vascular smooth muscle cells (FIG. 4). While patches reconstituted with recombinant PKG, or PKG plus scrambled SW329-358 peptide showed no significant increase in $NP_O$ over non-PKG controls, SW329-358 peptide increased $NP_O$, similar to cGMP.

Direct communication between regulatory and catalytic elements is not without precedent in AGC kinases. In PKA, there are at least four major sites of contact between the R and C subunits, with CNB domain A providing the largest docking surface for the C subunit (Boettcher et al., 2011; Kim et al., 2007). Likewise, in PKC βII, the conserved NH motif in the catalytic domain is clamped by the diacylglycerol-binding C1B domain until fully activated (Leonard et al., 2011). While these interactions highlight the diversity of interdomain complementarity among AGC kinase family members, they also demonstrate clear commonalities in their mechanisms of regulation.

This crystal structure provides the first atomic view of PKG and provides a new platform for understanding the allosteric regulation of the holoenzyme complex. The overall fold of $PKG^{78-355}$ is surprising, in that a previously uncharacterized allosteric interface promotes a novel means of communication between $PKG^{78-355}$ protomers wherein the catalytic domain can be tethered between inactive and active states. The crossing of switch helices between protomers (FIG. 10B) suggests that the catalytic domain from one protomer is regulated in part by the regulatory domain of the other protomer.

Based on the structures described herein, a class of compounds having therapeutic activity has been discovered. These compounds, referred to herein as cGMP independent PKG activators, are able to activate PKG in the absence of cGMP. The cGMP independent PKG activators include peptides, nucleic acids, and small molecules. In some embodiments a cGMP independent PKG activator does not include BR4979 or BR4980.

In certain embodiments, the cGMP independent PKG activators are peptides, antibodies or antigen-binding fragments that bind to the PKG activation domain. The peptides, antibodies or fragments thereof may be selected for the ability to bind the activation domain of PKG in the absence of cGMP.

In some embodiments the cGMP independent PKG activator is a peptide of 15-30 amino acids in length. Thus, the invention includes peptides and peptide mimetics that bind to the nest region. These peptides maybe structurally similar to the knob. For instance, an isolated peptide comprising $X_1X_2X_3X_4X_5X_6X_7X_8$ (SEQ ID NO: 8), wherein each X is an amino acid, and wherein the peptide binds to a nest region according to the invention. X refers to any amino acid, naturally occurring or modified. In some instances the peptide comprises FFANL (SEQ ID NO. 9). In some embodiments the Xs referred to the in SEQ ID NO: 8 have the following values:

$X_1$ is Ala, Gly, Leu, Ile, Val, Cys, Ser, Thr, or Pro
$X_2$ is Ala, Gly, Leu, Ile, Val, Cys, Ser, Thr, or Pro
$X_3$ is Phe, Tyr, or Trp
$X_4$ is Phe, Tyr, or Trp
$X_5$ is Ala, Gly, Leu, Ile, Val, Cys, Ser, Thr, or Pro
$X_6$ is Asn, Asp, Glu, Gln, Ser, or Thr
$X_7$ is Leu, Ile, Val, or Ala
$X_8$ is Lys Arg, Glu, His, Asp, Gln, Ser, Thr, or Tyr

In other embodiments the Xs referred to the in SEQ ID NO: 8 have the following values:
$X_1$ is Ala, Gly, Leu, Ile, or Val
$X_2$ is Ala, Gly, Leu, Ile, or Val
$X_3$ is Phe, Tyr, or Trp
$X_4$ is Phe, Tyr, or Trp
$X_5$ is Ala, Gly, Leu, Ile, or Val
$X_6$ is Asn, Asp, or Glu,
$X_7$ is Leu, Ile, Val, or Ala
$X_8$ is Lys or Arg The peptide preferably is $X_1X_2$FFANL$X_8$ (SEQ ID NO: 10), such that $X_1X_2$, and $X_8$ are any amino acid and may be Ala of Lys.

The minimal peptide length for binding the nest is 5 and preferably 8 amino acids. However, there can be overhanging amino acids on either side of the core structure. For some well-studied peptides, it is known that additional overhanging amino acids on both the N and C termini can augment binding. Thus the peptide may be 9 amino acids in length or it may be longer. For instance, the peptide may have additional amino acids at the N and/or C terminus. The amino acids at either terminus may be anywhere between 1 and 100 amino acids. In some embodiments the peptide includes 1-50, 1-20, 1-15, 1-10, 1-5 or any integer range there between. When the peptide is referred to as "N-AAFFANLK-C" (SEQ ID NO: 7) the —C and —N refer to the terminus of the peptide and thus the peptide is only 8 amino acids in length. However the 8 amino acid peptide may be linked to other non-peptide moieties at either the —C or —N terminus or internally.

Examples of specific peptides that are useful as a cGMP independent PKG activator include DVSNKAYEDAE-AKAKYEAEAAFFANLKLSD (SEQ ID NO. 4); DVSNKAYEDAEAKAKYEAEAAFFANLK (SEQ ID NO. 5); DVSNKAYEDAEAKAKYEAEAAFF (SEQ ID NO. 41); and AAFFANLK (SEQ ID NO. 7). Peptides encompassing conservative substitutions of SEQ ID NOs.4, 5, 41, and 7 are also encompassed within the invention. Other peptides can easily be identified by the skilled artisan using computer modeling and/or peptide screening, such as peptide library screens using the information provided herein.

Guidance as to appropriate amino acid substitutions that do not affect biological activity of the polypeptide of interest may be found in the model of Dayhoffet al. (1978) in Atlas of Protein Sequence and Structure (Natl. Biomed. Res. Found., Washington, D.C.), and Betts and Russell, Bioinformatics for Geneticists, chapter 14, 2003, herein incorporated by reference. Conservative substitutions, such as exchanging one amino acid with another having similar properties, may be preferred. Examples of conservative substitutions include, but are not limited to, Gly,Ala; Val,Ile,Leu; Asp,Glu; Lys,Arg; Asn,Gln; and Phe,Trp,Tyr or alternatively within the following classifications: hydrophobic (Ala, Ile, Pro, Val, Phe, Trp, Tyr), hydrophobic aliphatic side chains (Ala, Ile, Pro, Val), hydrophobic aromatic side chains (Phe, Trp, Tyr), polar amino acids (Asn (negative), Glu (negative), Lys (positive), Arg (positive), His (neutral), Asp (neutral), Gln (neutral), Ser (neutral), Thr (neutral), Tyr (neutral)), and small amino acids (Ala, Cys, Gly, Pro, Ser, Thr).

The peptide has a minimum length of 9 amino acids. In some embodiments it has a length of 9-20 amino acids. The peptide may be cyclic or non-cyclic. In some embodiments the peptide is PEGylated. In other aspects the invention is an isolated peptide comprising SEQ ID NO. 7.

The amino acids may be naturally occurring amino acids as well as non-naturally occurring amino acids. Naturally occurring amino acids are generally α-amino acids because the amino group is attached to the first carbon atom after the COOH group. Conventionally a peptide is numbered from the N terminal to C terminal end.

A composition of a peptide of the invention and a carrier is provided in other aspects. In some embodiments the carrier is a liposome, such as a stealth liposome. In other embodiments the carrier is a particle, for instance, a nanoparticle or a low density particle. In other embodiments the carrier is a transmucosal absorption enhancer.

The peptides may also be linked to other molecules. The two or more molecules may be linked directly to one another (e.g., via a peptide bond); linked via a linker molecule, which may or may not be a peptide; or linked indirectly to one another by linkage to a common carrier molecule, for instance.

Thus, linker molecules ("linkers") may optionally be used to link the peptide to another molecule. Linkers may be peptides, which consist of one to multiple amino acids, or non-peptide molecules. Examples of peptide linker molecules useful in the invention include glycine-rich peptide linkers (see, e.g., U.S. Pat. No. 5,908,626), wherein more than half of the amino acid residues are glycine. Preferably, such glycine-rich peptide linkers consist of about 20 or fewer amino acids.

Linker molecules may also include non-peptide or partial peptide molecules. For instance the peptide may be linked to other molecules using well known cross-linking molecules such as glutaraldehyde or EDC (Pierce, Rockford, Ill.). Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. General methods for cross-linking molecules have been reviewed (see, e.g., Means and Feeney, *Bioconjugate Chem.*, 1: 2-12 (1990)).

Homobifunctional cross-linker molecules have two reactive sites which are chemically the same. Examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., discuccinimyidyl suberate, dithiobis(succinimidyl propionate), and soluble bis-sulfonic acid and salt thereof (see, e.g., Pierce Chemicals, Rockford, Ill.; Sigma-Aldrich Corp., St. Louis, Mo.).

Preferably, a bifunctional cross-linker molecule is a heterobifunctional linker molecule, meaning that the linker has at least two different reactive sites, each of which can be separately linked to a peptide or other molecule. Use of such heterobifunctional linkers permits chemically separate and stepwise addition (vectorial conjunction) of each of the reactive sites to a selected peptide sequence. Heterobifunctional linker molecules useful in the invention include, without limitation, m-maleimidobenzoyl-N-hydroxysuccinimide ester (see, Green et al., *Cell*, 28: 477-487 (1982); Palker et al., *Proc. Natl. Acad. Sci (USA)*, 84: 2479-2483 (1987)); m-maleimido-benzoylsulfosuccinimide ester; γ-maleimidobutyric acid N-hydroxysuccinimide ester; and N-succinimidyl 3-(2-pyridyl-dithio)propionate (see, e.g., Carlos et al., *Biochem. J.*, 173: 723-737 (1978); Sigma-Aldrich Corp., St. Louis, Mo.).

The carboxyl terminal amino acid residue of the peptides described herein may also be modified to block or reduce the reactivity of the free terminal carboxylic acid group, e.g., to prevent formation of esters, peptide bonds, and other reactions. Such blocking groups include forming an amide of the carboxylic acid group. Other carboxylic acid groups that may be present in polypeptide may also be blocked, again provided such blocking does not elicit an undesired immune reaction or significantly alter the capacity of the peptide to specifically function.

The peptide for instance, may be linked to a PEG molecule. Such a molecule is referred to as a PEGylated peptide. The peptides useful herein are isolated peptides.

In further embodiments, the peptide is an antibody or antigen biding fragment thereof against the activation domain of PKG. An antibody or antigen-binding fragment thereof is selected from the group consisting of IgG1, IgG2, IgG3, IgG4, IgM, IgA1, IgA2, IgAsec, IgD, IgE or has immunoglobulin constant and/or variable domain of IgG1, IgG2, IgG3, IgG4, IgM, IgA1, IgA2, IgD or IgE. In other embodiments, the antibody is a bispecific or multispecific antibody. In still other embodiments, the antibody is a recombinant antibody, a polyclonal antibody, a monoclonal antibody, a humanized antibody or a chimeric antibody, or a mixture of these. In particularly preferred embodiments, the antibody is a human antibody, e.g., a monoclonal antibody, polyclonal antibody or a mixture of monoclonal and polyclonal antibodies. In still other embodiments, the antibody is a bispecific or multispecific antibody. Preferred antigen-binding fragments include a Fab fragment, a F(ab')$_2$ fragment, and a F$_V$ fragment CDR3. Antibodies can be generated by injecting an animal, preferably a rabbit or goat or mouse, with the PKG activation domain.

In order to prepare polyclonal antibodies, fusion proteins containing the complete or defined fragments of the PKG activation domain protein can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, protein can be isolated from cultured cells expressing the protein. Following booster injections at bi-weekly intervals, the rabbits or other laboratory animals are then bled and the sera isolated. The sera can be used directly or purified prior to use, by various methods including affinity chromatography, Protein A-Sepharose, Antigen Sepharose, Anti-mouse-Ig-Sepharose. The sera can then be used to probe protein extracts run on a polyacrylamide gel to identify the PKG activation domain. Alternatively, synthetic peptides can be made to the antigenic portions of the protein and used to inoculate the animals.

To produce monoclonal PKG activation domain antibodies, mice are injected multiple times, the mice spleens are removed and resuspended in a phosphate buffered saline (PBS). The spleen cells serve as a source of lymphocytes, some of which are producing antibody of the appropriate specificity. These are then fused with a permanently growing myeloma partner cell, and the products of the fusion are plated into a number of tissue culture wells in the presence of a selective agent such as HAT. The wells are then screened to identify those containing cells making useful antibody by ELISA. These are then freshly plated. After a period of growth, these wells are again screened to identify antibody-producing cells. Several cloning procedures are carried out until over 90% of the wells contain single clones which are positive for antibody production. From this procedure a stable line of clones is established which produce the antibody. The monoclonal antibody can then be purified by affinity chromatography using Protein A Sepharose, ion-exchange chromatography, as well as variations and combinations of these techniques.

For antibodies to be used in therapy in humans, they preferably are 'humanized'. Humanization of antibodies involves replacing native mouse sequences with human sequences as to lower the chance of an immune response once the therapeutic antibody is introduced into humans.

Computational techniques can be used to screen, identify, select, and design compounds capable of binding to the activation domain of PKG and functioning as cGMP independent PKG activators. In particular, computational techniques can be used to identify or design ligands, such as agonists and/or antagonists, that associate with the activation domain of PKG. Once identified and screened for biological activity, these agonists, antagonists, and combinations thereof, may be used therapeutically, for example, to increase PKG activity. Data stored in a machine-readable storage medium that is capable of displaying a graphical three-dimensional representation of the structure of the potential therapeutic compound or a structurally homologous molecule or molecular complex, as identified herein, or portions thereof may thus be advantageously used for drug discovery. The structure coordinates of the potential therapeutic compounds are used to generate a three-dimensional image that can be computationally fit to the three-dimensional image of the activation domain of PKG. The three-dimensional molecular structure encoded by the data in the data storage medium can then be computationally evaluated for its ability to associate with the potential therapeutic compound. When the molecular structures encoded by the data is displayed in a graphical three-dimensional representation on a computer screen, the protein structure can also be visually inspected for potential association with the potential therapeutic compound.

One embodiment of the method of drug design involves evaluating the potential association of a candidate therapeutic compound with the activation domain of PKG. The method of drug design thus includes computationally evaluating the potential of a selected ligand to associate with any of the molecules or molecular complexes set forth above. This method includes the steps of: (a) employing computational means, for example, such as a programmable computer including the appropriate software known in the art or as disclosed herein, to perform a fitting operation between the potential therapeutic compound and the activation domain of PKG and (b) analyzing the results of the fitting operation to quantify the association between the potential therapeutic compound and the activation domain of PKG. Several methods can be used to screen potential therapeutic compounds for the ability to associate with the activation domain of PKG. Selected potential therapeutic compounds may be positioned in a variety of orientations associating with the activation domain of PKG. This may be accomplished using software such as QUANTA (Molecular Simulations, Inc., San Diego, Calif., USA.) and SYBYL (TRIPOS, St. Louis, Mo., USA), followed by energy minimization and molecular dynamics with standard molecular mechanics force fields, such as CHARMM (Molecular Simulations, Inc., San Diego, Calif., USA) and AMBER (P. A. Kollman, University of California at San Francisco, San Francisco, Calif., USA).

Any of the biological or biochemical functions mediated by the activation domain of PKG can be used as an endpoint assay to identify an agent that modulates PKG activity (a putative therapeutic compound). The assays may include all of the biochemical or biochemical/biological events described herein, in the references-cited herein, incorporated by reference for these endpoint assay targets, and other functions known to those of ordinary skill in the art or that can be readily identified. Compounds can be identified through cellular assays. Cellular assays may involve, for instance, expressing the activation domain of PKG in cells and testing a variety of compounds for their ability to bind to the expressed peptide. The assay may be performed with labeled compounds, facilitating identification of the compound that binds. In another embodiment a biological readout can be used to identify a putative therapeutic compound. Biological assays will allow for the identification of both agonists and antagonists or inhibitors. Competition binding assays may also be used to discover compounds that interact with the activation domain of PKG (e.g. binding partners and/or ligands). Thus, a compound is exposed to the activation domain of PKG under conditions that allow the compound to bind or to otherwise interact with the polypeptide. A peptide or antibody or fragment thereof against the activation domain of PKG may be added to the mixture. If the test compound interacts with the activation domain of PKG, it decreases the amount of peptide or antibody that can bind to the activation domain of PKG. To perform cell free drug screening assays, it is sometimes desirable to immobilize the activation domain of PKG, or its target molecule to facilitate separation of complexes from uncomplexed forms of one or both of the proteins, as well as to accommodate automation of the assay. Agents that modulate the activation domain of PKG can be identified using one or more of the above assays, alone or in combination. It is generally preferable to use a cell-based or cell free system first and then confirm activity in an animal or other model system. Such model systems are well known in the art and can readily be employed in this context.

To unlock the therapeutic potential of the activation domain of PKG, the structure of the activation domain of PKG has been elucidated. The invention presented herein discloses the materials and methods that were used to determine the structure and mechanism of function of the activation domain of PKG. The invention also encompasses compositions and methods of use of native activation domains of PKG as well as modified activation domains of PKG having at least one deletion or substitution from a native activation domain of PKG, for instance, when it is desirable to compete with a naturally occurring PKG. As used herein, a native activation domain of PKG is a naturally occurring form of PKG including two cGMP binding domains, a hinge region, and a switch helix. The native activation domain of PKG may have the sequence of any naturally occurring PKG, but preferably has the sequence of a human PKG.

The activation domain of PKG may be an isolated peptide. An isolated peptide or molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation or be mixed with some of the components with which it is associated in nature, the molecular species may comprise only a small percentage by weight of the preparation. The molecular species is nonetheless substantially pure in that it has been substantially separated from the substances with which it may be associated in living systems.

The activation domain of PKG may be in the context of, or separate from, the full length PKG or portions thereof. If the activation domain of PKG is in the context of the PKG it may form a full length or partial PKG. The full length or partial PKG may include the native sequence or may include insertions, deletions or substitutions. When the peptide consists of the activation domain of PKG it is not found in the context of a partial or full length PKG.

Modified activation domains of PKG having at least one substitution, deletion or insertion are also useful according to the invention. As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants.

Methods for making amino acid substitutions, additions or deletions are well known in the art. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions and properties of amino acids which lead to their definition as polar, non-polar or acidic.

The modified activation domains of PKG having at least one substitution, deletion or insertion have, in some embodiments, a native conformation. A native conformation as used herein refers to a tertiary structure that is similar to the tertiary structure of native activation domain of PKG. The tertiary structure of modified or native activation domains of PKG can be assessed using structural analysis such as crystallography or by functional analysis, such as binding and/or activity assays and NMR spectroscopy.

Crystallographic data can be obtained by performing crystallographic analysis on crystals of the activation domain of PKG using for instance, the methods described in the Examples. Alternatively crystals can be grown by various methods, such as, for example, sitting or hanging drop vapor diffusion. In general, crystallization can be performed at a temperature of from about 4° C. to about 60° C. The activation domain of PKG can be crystallized from a solution including NaCl, $MgCl_2$, Tris buffer and polyethylene glycol (PEG). The solution can include a precipitant, such as ammonium sulfate. Structural data describing a crystal can be obtained, for example, by X-ray diffraction. X-ray diffraction data for the crystals can be collected by a variety of means in order to obtain structural coordinates. Suitable X-ray sources include rotating anode and synchrotron sources (e.g., NSLS, Brookhaven, N.Y.). The X-ray diffraction data can be used to construct an electron density map of the activation domain of PKG. Creation of an electron density map typically involve using information regarding the phase of the X-ray scatter. Methods for calculating phase from X-ray diffraction data, include, without limitation, multiwavelength anomalous dispersion (MAD), multiple isomorphous replacement (MIR), multiple isomorphous replacement with anomalous scattering (MIRAS), reciprocal space solvent flattening, molecular replacement, and single isomorphous replacement with anomalous scattering (SIRAS), or a combination thereof. These methods generate phase information by making isomorphous structural modifications to the native protein, such as by including a heavy atom or changing the scattering strength of a heavy atom already present, and then measuring the diffraction amplitudes for the native protein and each of the modified cases. If the position of the additional heavy atom or the change in its scattering strength is known, then the phase of each diffracted X-ray can be determined by solving a set of simultaneous phase equations. The location of heavy atom sites can be identified using a computer program, such as SHELXS, (Sheldrick, Institut Anorg. Chemie, Gottingen, Germany) or Sharp (Global Phasing, Cambridge, UK) and diffraction data can be processed using computer programs such as MOSFLM, SCALA, SOLOMON, ("The CCP4 Suite: Programs for Protein Crystallography," 1997, Acta Crystallogr. Sect. D, 54, 905-921; deLa Fortelle et al. 1997, Meth. Enzym. 276, 472-494) and HKL2000 (HKL Research, Charlottesville, Va.). Upon determination of the phase, an electron density map of the complex can be constructed.

The electron density map can subsequently be used to derive a representation of a polypeptide, a complex, or a fragment of a polypeptide or complex by fitting a three-dimensional model of a polypeptide or complex into the electron density map.

The conformation of the activation domain of PKG may also be assessed by whether the activation domain of PKG is able to bind to compounds that the native activation domain of PKG binds to. The binding of the activation domain of PKG to cGMP may be determined according to standard procedures.

Thus the compounds of the invention are useful for treating subjects having a PKG deficient condition as well as other disorders described herein. A "subject" shall mean a human or vertebrate mammal including but not limited to a dog, cat, horse, cow, pig, sheep, goat, or primate, e.g., monkey.

Thus, in some aspects the invention is a method of treating a PKG deficient condition in a subject. The method involves administering to the subject a therapeutically effective amount of a cGMP independent PKG activator. A PKG deficient condition includes but is not limited to cardiovascular disorders, hypoxia, spinal cord injury, and stroke.

The compounds of the invention are useful in effective amounts. The term effective amount refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular cGMP independent PKG activator being administered, the size of the subject, or the severity of the disease or condition. One of ordinary skill in the art can empirically determine the effective amount of a particular cGMP independent PKG activator and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug. "Dose" and "dosage" are used interchangeably herein.

Generally, daily oral doses of active compounds will be from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the cGMP independent PKG activator can be administered to a subject by any mode that delivers the cGMP independent PKG activator to the desired surface. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the cGMP independent PKG activator can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the cGMP independent PKG activator or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the cGMP independent PKG activator may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the cGMP independent PKG activator either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from presurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the cGMP independent PKG activator. The cGMP independent PKG activator is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of cGMP independent PKG activator. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, 1990, Science 249, 1527-1533, which is incorporated herein by reference.

The cGMP independent PKG activator and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a cGMP independent PKG activator and optionally therapeutic agents included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the cGMP independent PKG activator, may be provided in particles. Particles as used herein means nano or microparticles (or in some instances larger) which can consist in whole or in part of the cGMP independent PKG activator or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the cGMP independent PKG activator in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by Sawhney et. al., 1993, Macromolecules 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The cGMP independent PKG activator can be combined with other therapeutic agents. The cGMP independent PKG activator and other therapeutic agent may be administered simultaneously or sequentially. When the other therapeutic agents are administered simultaneously they can be administered in the same or separate formulations, but are administered at the same time. The other therapeutic agents are administered sequentially with one another and with cGMP independent PKG activator, when the administration of the other therapeutic agents and the cGMP independent PKG activator is temporally separated. The separation in time between the administration of these compounds may be a matter of minutes or it may be longer.

Thus, the cGMP independent PKG activator may also be administered in conjunction with an another therapy, such as a cGMP dependent PKG activator. A cGMP dependent PKG activator is a compound that can activate PKG when cGMP is bound to PKG. These compounds include for instance PDE inhibitors and NO-donors. The PDE inhibitor may be, for example, sildenafil citrate, vinpocetine, EHNA, anagrelide, enoximone, milrinone, mesembrine, rolipram, ibudilast, piclamilast, luteolin, drotaverine, roflumilast, tadalafil, vardenafil, udenafil, avanafil, or papaverine. The NO-donor may be, for example, isosorbide dinitrite, Diazeniumdiolates, NONOates, S-Nitrosothiols, NO hybrid drugs, or Zeolites. 4. The compounds of the invention may also be administered with cGMP to the subject.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Bacterial Protein Expression and Purification:
DNA for bovine PKG Iα encoding amino acids $Q^{78}$-$K^{355}$ was amplified by PCR using the primers 50-CGGGATCCAT-GCAGGCATTCCGGAAGTTC-30 (sense, SEQ ID NO. 42) and 50-GGAATTCCTACTACTTCAGGTTGGCGAAG-30 (antisense, SEQ ID NO. 43). The PCR product was digested with BamHI and EcoRI and ligated into pRSET-A (Invitrogen) in frame with the N-terminal 6x-His tag. The plasmid was transformed into *E. coli* BL21 and 5 ml starter cultures in LB were allowed to grow to OD600=0.6 at 37 C, 300 RPM in the presence of 50 mg/ml Ampicillin. One liter of Overnight Express (Novagen) media was inoculated 1:1000 in 4 liter baffled flasks with the mid-log starter prep and grown at 25° C., 300 RPM for 16-24 hr. Bacteria were harvested by centrifugation at 5K RPM for 10 min at 4° C., and pellets were stored at −80° C. Pellets were resuspended in 5 ml/gram of 50 mM MES (pH 6.8), 100 mM NaCl, 5 mM $MgCl_2$, 3 mM TCEP, 5% glycerol (Buffer A) plus protease inhibitors. Cells were lysed at 1200 psi using a French pressure cell. Homogenates were clarified via centrifugation at 15K RPM for 90 min at 4° C. and recombinant PKG Iα$^{78-355}$ was purified from the supernatants on a Profinia protein purification system (Biorad) using the native IMAC protocol. Eluted protein was subjected to three rounds of dialysis in 2 liters of buffer A at 4° C. A secondary purification step was performed on an AKTAprime FPLC system by passing Ni2+-purified protein over a HiLoad 16/60 Superdex 75 (GE Healthcare) gel filtration column and collecting 1 ml fractions in Buffer A. Protein homogeneity was assessed via SDS-PAGE and Coomassie staining. Desired fractions were pooled and concentrated using 10K MWCO centrifugal concentrators (Sartorius). Typical yields were 100 mg purified protein per liter of media.

Crystallization, Data Collection, and Model Refinement:
Sparse matrix kits from Hampton Research were used to screen initial crystal growth conditions. Crystals used for data collection were grown via hanging drop vapor diffusion in 2.2 M $(NH_4)_2SO_4$, 100 mM Tris (pH 8.0), 0.2% MPD at a protein concentration of 25-35 mg/ml at 20° C. Crystals were cryoprotected for 10-30 min in 2 M $Li_2SO_4$, 100 mM Tris (pH 8.0), 0.2% MPD and flash frozen in liquid N2. 2.5 Å diffraction data were collected at beamline 8.2.1 at the Advanced Light Source, Lawrence Berkeley National Laboratory. HKL2000 was used for data processing and scaling (Minor, 1997). Phases were generated with the program Phaser (McCoy et al., 2007) using the PKA regulatory domain (PDB ID 1RGS) as a search model. Crystals grew in the C2 space group with two molecules per asymmetric unit. The PKG Iα$^{78-355}$ model was manually built into electron density using the programs TURBO-FRODO (Roussel and Cambillau, 1991) and Coot (Emsley et al., 2010). CNS (Brunger et al., 1998) was used for structure refinement. Publication-quality images were generated using Pymol (The PyMOL Molecular Graphics System, Version 1.2r3pre, Schrodinger, LLC). Interface and assembly measurements of symmetry mates were calculated using the protein interfaces, surfaces, and assemblies service PISA at European Bioinformatics Institute (Krissinel and Henrick, 2007).

Deuterium on Exchange:
All deuterium exchange reactions were performed on ice, in a 4° C. cold room. Exchange reactions were initiated by adding 6 ml buffered $D_2O$ to 2 ml purified PKG Iα$^{78-355}$ at 7 mg/ml. At the appropriate time points exchange was quenched by adding 12 ml 1.6MGuHCl, 0.8% formic acid. In addition, nondeuterated samples were prepared by incubating the protein in buffered $H_2O$. Fully deuterated samples were prepared by incubating the protein in D20 buffer containing 1% formic acid overnight at room temperature. The samples were frozen on dry ice and stored at −80° C. until analysis by mass spectrometry. Samples were manually thawed on wet ice and immediately analyzed by LC-MS. Procedures for pepsin digestion for DXMS have been described previously (Burns-Hamuro et al., 2005; Hamuro et al., 2004; Pantazatos et al., 2004; Spraggon et al., 2004). Briefly, the samples were passed through an immobilized pepsin column and the protease-generated peptides were collected on a C18 HPLC column. The peptides were eluted from the C18 column and the effluent was directed to a Thermo Finnigan LCQ electrospray ion trap type mass spectrometer with data acquisition in either MS1 profile mode or data dependent MS2 mode. The pepsin-generated peptides from the MS/MS data sets were identified using SEQUEST (Thermo Finnigan Inc.), followed by analysis using customized DXMS data reduction software (Siena Analytics Inc., Modesto, Calif.). Corrections for back exchange were made through measurement of loss of deuterium from fully deuterated samples. Deuterium incorporation for each peptide was calculated using the methods of Zhang and Smith (1993):

$$\text{deuteration level}(\%) = \frac{m(p) - m(N)}{m(F) - m(N)} \times 100$$

where m(P), m(N), and m(F) are the centroid value of the partially deuterated, nondeuterated, and fully deuterated peptide, respectively. The experiments were performed twice, and the reported results are the average of the two experiments.

Cyclic Nucleotide Analysis:

To confirm the copurification of cAMP, purified PKG$^{78-355}$ was incubated on ice in a 1:1 ratio of acetonitrile. The extract was clarified via centrifugation at 4° C. and the supernatant was subjected to UV-spectroscopy. The extract had a single peak with a 1 max of 258 nm and lacked the characteristic cGMP shoulder. The same extract was subjected to HPLC analysis using a Merck Hitachi HPLC system comprising a L-2130 pump, a L-2400 UV detector, a L-2350 column oven, and a L-2200 autosampler, and data were processed with EZChrom Elite evaluation software (3.2.1). Isocratic runs were performed at 30° C. on a RP-18 reversed phase silica column (250 3 4 mm, ODS A, YMC) with 2.5% isopropanol and 25 mM triethylammonium formate buffer (pH 6.9) with a flow of 1 ml/min at 255 nm.

Mammalian Protein Expression:

WT PHG Iα was cloned into pcDNA 3.1 using BamHI and EcoRI. Mutations were made using QuickChange site-directed mutagenesis (Agilent Technologies, Santa Clara, Calif.) per manufacturer's recommendations. HEK293 cells grown in 10 cm dishes were transfected for 5 hr using Metafectene (Biontex, San Diego, Calif.) at a ratio of 20 mg DNA per 60 ml lipid. Sixty hours after transfection cells were harvested by scraping into PBS, 2 mM benzamidine-HCl, 200 mM EDTA. Protein concentration was determined by the Bradford method and stocks were stored in 50% glycerol at −20° C.

Kinetic Analysis:

Determination of activation constants was performed using a [γ-$^{32}$P]-ATP transfer assay as previously reported (Ruth et al., 1991; Tegge et al., 1995). Briefly, 0.5 mg of wild-type or mutant protein from PKG-transfected HEK293 cells was incubated in buffer with various concentration of cGMP in the presence of [g-32P]-ATP and the PKG-specific peptide substrate TQAKRKK SLAMA (SEQ ID NO 3) (Dostmann et al., 1999). Aliquots, spotted on P81 Whatman paper were subjected to scintillation counting. All experiments were performed in the presence of the PKA-specific inhibitor, PKI$^{5-24}$ (70 nM) to suppress endogenous PKA activity. Mock-transfected cells did not show any activity.

Example 1

Overall Fold of PHG Iα$^{78-355}$

Crystals grew in the C2 space group with two molecules per asymmetric unit. Superimposition of Ca atoms from the two molecules sites gave an average root mean square deviation (rmsd) of 0.882. Initial phases were attained by molecular replacement using the CNB-A domain of PKA RIa (PDB ID 1RGS) as a search model. The structure was refined to 2.5 Å with working and free-R factor values of 0.22 and 0.28, respectively as shown in Table 1. Each protein molecule in the asymmetric unit contained 278 amino acids, 1 cAMP molecule, and 2 phosphates.

TABLE 1

Data Collection and Refinement Statistics

|  | PKG Iα$^{78-355}$ |
| --- | --- |
| Data collection |  |
| Space group | C2 |
| Cell dimensions (Å) |  |
| A | 180.2 |
| B | 66.0 |
| C | 81.6 |
| β(°) | 113.8 |
| No. of molecule per asymmetrical unit | 2 |
| Resolution (Å) | 2.50 |
| R$_{merge}$ | 0.085 (0.52) |
| Completeness (%) | 97.9 (93.5) |
| I/sigma | 18.7 (1.9) |
| No. reflections | 32.166 |
| Refinement |  |
| Resolution (Å) | 50.0-2.50 |
| R$_{work}$/R$_{free}$ (%) | 22.1/27.7 |
| No. of protein residues | 556 |
| No. of ligands/ions | 4 |
| No. of water molecules | 207 |
| Rmsd |  |
| Bond lengths (Å) | 0.008 |
| Bond angles (°) | 1.4 |
| Ramachandran angles (%) |  |
| Most favored | 83.3 |
| Disallowed | None |

Values in parentheses are for highest-resolution shell.

Figure 5A:
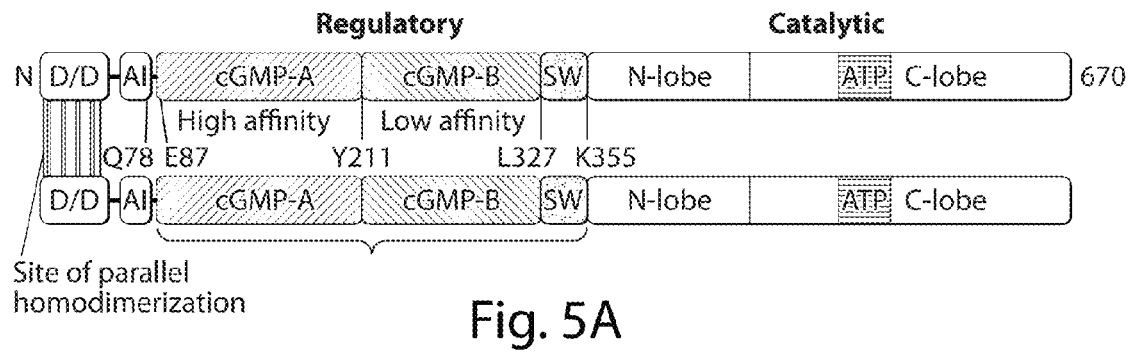
FIG. 5: PKG Iα: Domain Organization and General Architecture of $PKG^{78-355}$ (A) D/D: docking and dimerization domain; AI: autoinhibitory domain; cGMP-A/B: cGMP binding sites A and B; SW: switch helix. Bars at the N terminus indicate site of parallel homodimerization. (B) Overall fold of $PKG^{78-355}$.
Figure 5B:
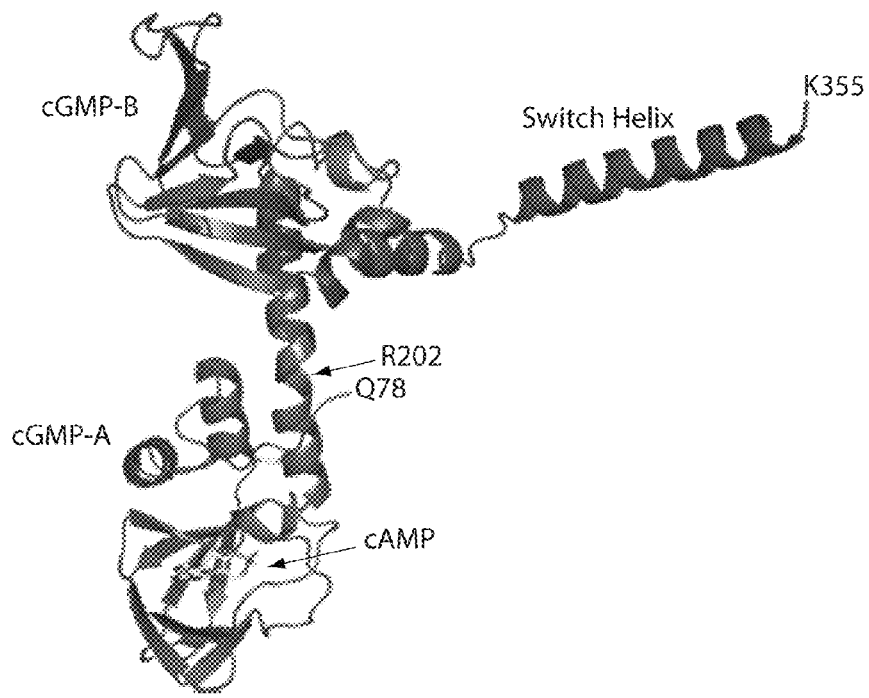
Figures 1, 12A:
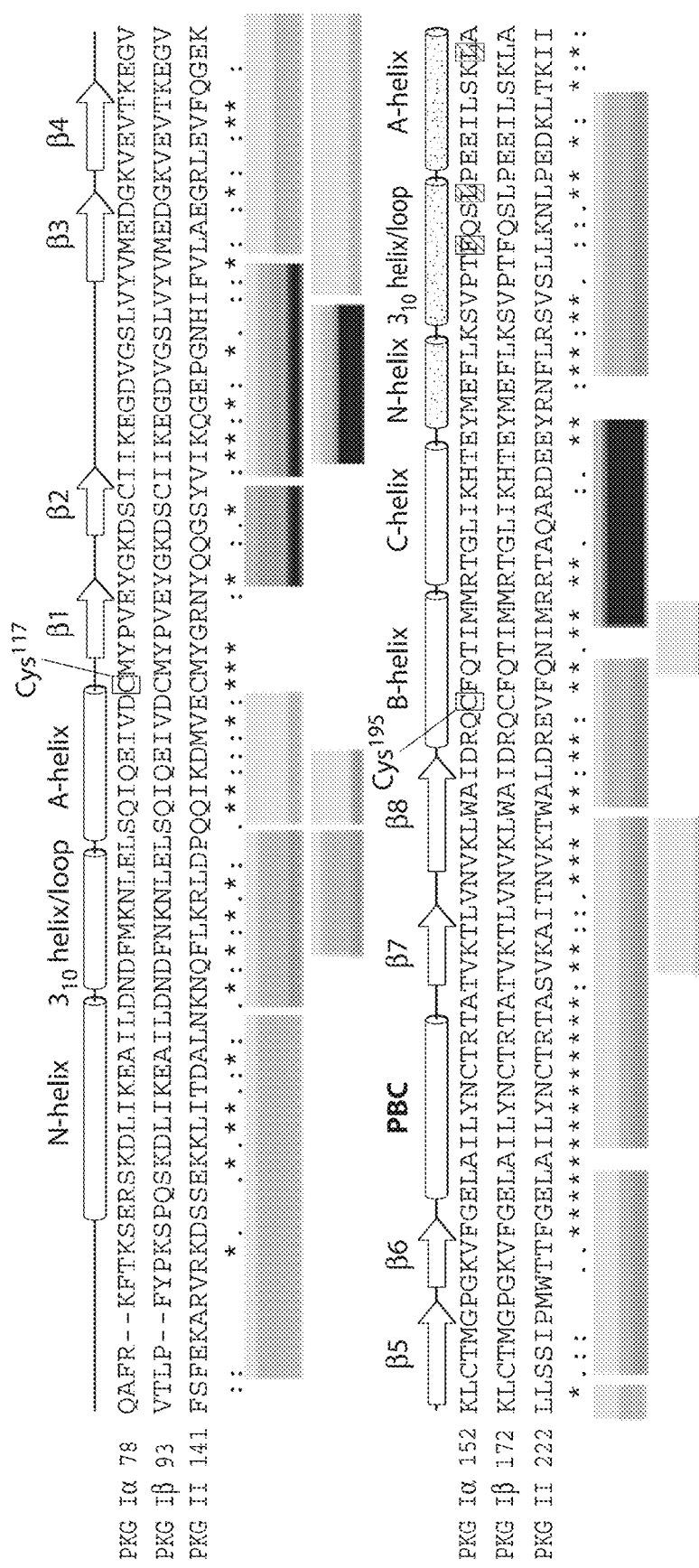
Figures 2, 12A:
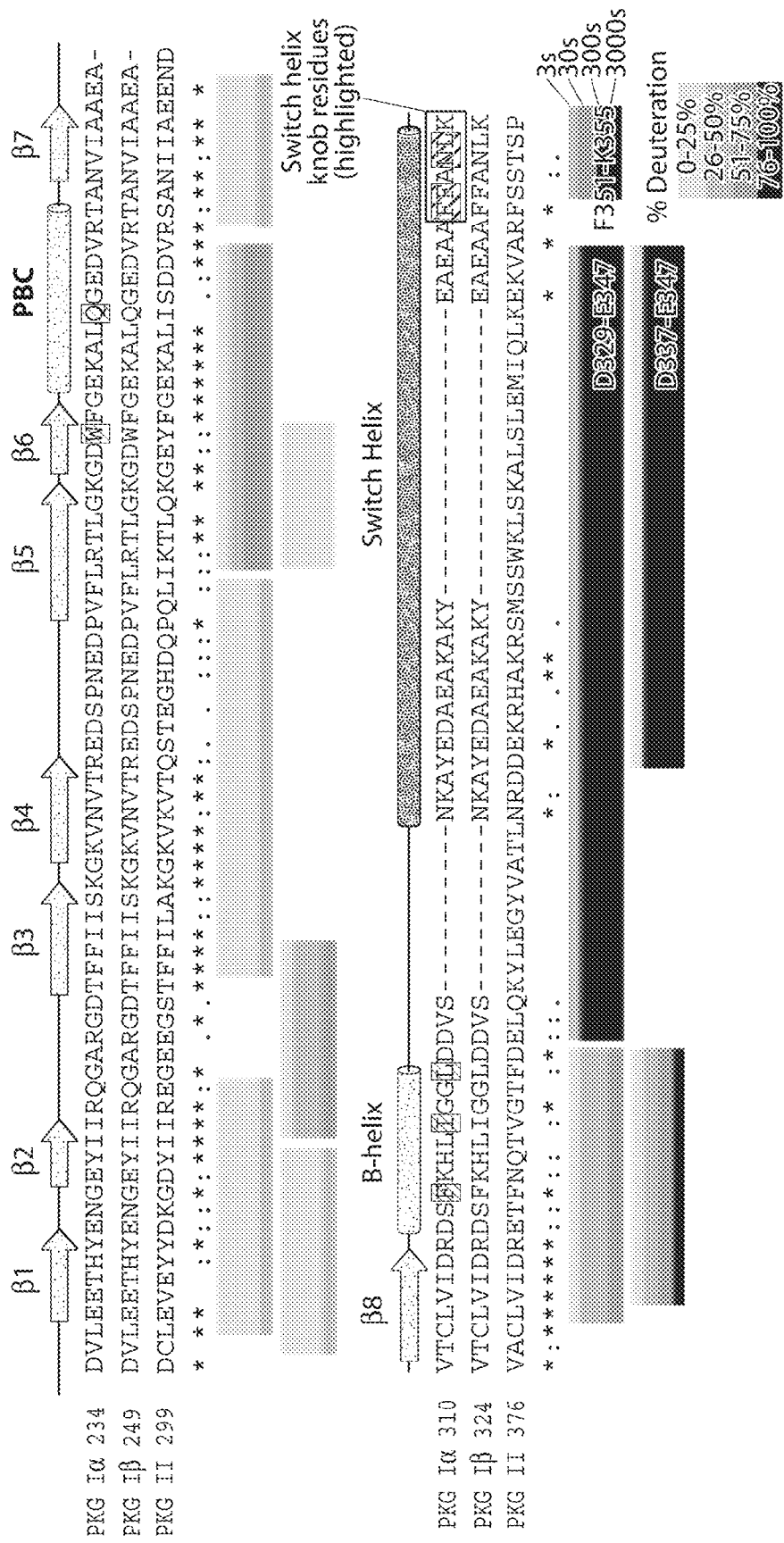
Figure 12B:
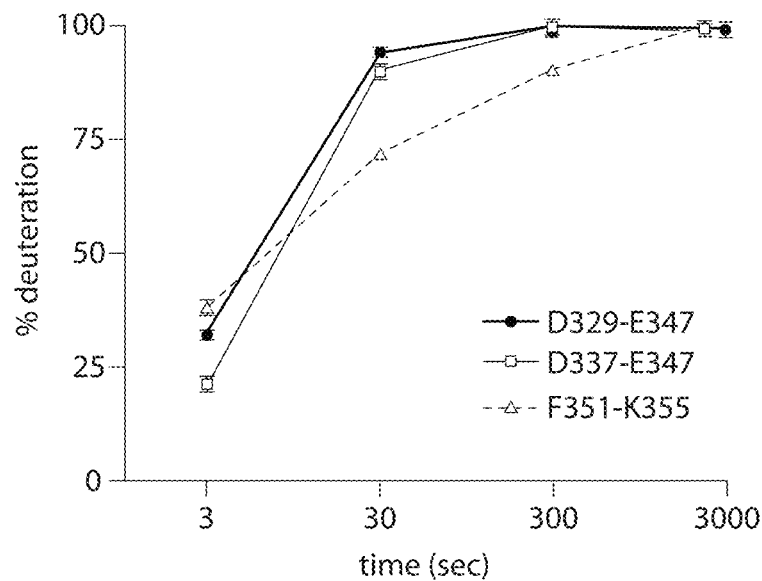
FIG. 12 DxMS for PKG$^{78-355}$. (A) Secondary structural features from the crystal structure of PKG Iα$^{78-355}$ are positioned above sequence alignment for PKG Iα, Iβ and II. Cys117 and Cys195 (boxed) form a disulfide bond in the A-domain. Individual residues that comprise the hydrophobic nest in the B domain are highlighted and switch helix knob residues are identified. DxMS results are presented under the sequence alignment. Percent deuteration was measured at four time points (3 s, 30 s, 300 s, 3000 s). SEQ ID NOs: 31, 32, 33, 34, 34, 35, 36, 37, 38, 39, 39, and 40 for each row from top to bottom. SEQ ID NOs: 1, 44 and 45 for full sequences of PKG Iα, PKG Iβ and PKG II, respectively. (B) Analysis of DxMS from switch helix peptides. Percent deuteration as a function of time for D$^{329}$-E$^{347}$ (●), D$^{337}$-E$^{347}$ (■) and F$^{351}$-K$^{355}$ (▲) is shown at the left with a summary of the initial rate of deuterium exchange from 3-30 seconds at the right.
Figure 12B:
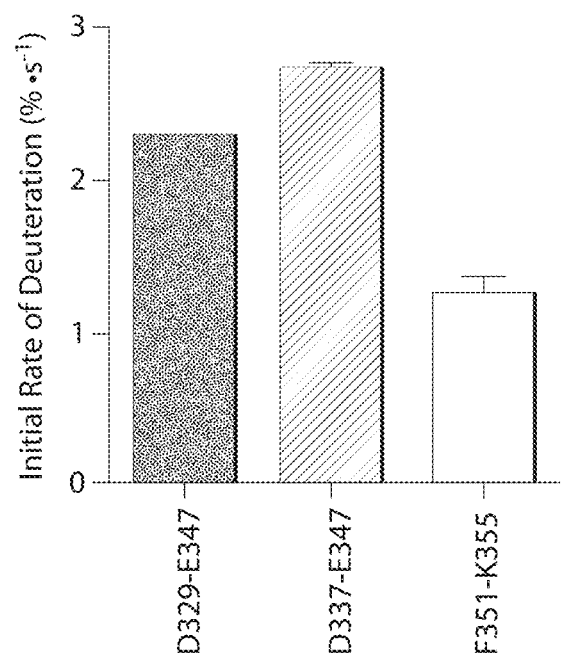

The overall fold presents both cGMP-binding domains of the PHG Iα regulatory domain. cGMP-binding site A (residues 87-210) begins following a loop in the "hinge region," for which we see clear backbone density, followed by cGMP-binding site B (residues 211-327) and a new helical subdomain we have termed switch helix (SW, residues 328-355) (FIG. 5B; FIG. 12A, secondary structural elements). FIG. 5 shows the domain organization and general architecture of PKG$^{78-355}$. FIG. 12 shows a DxMS for PKG$^{78-355}$. The secondary structural features from the crystal structure of PKG Iα$^{78-355}$ are positioned above sequence alignment for PKG Iα, Iβ and II. Cys117 and Cys195 form a disulfide bond in the A-domain. Residues that comprise the hydrophobic nest in the B domain are highlighted and switch helix knob residues are highlighted within the box. DxMS results are presented under the sequence alignment. Percent deuteration was measured at four time points (3 s, 30 s, 300 s, 3000 s). Percent deuteration as a function of time for $D^{329}$-$E^{347}$ (●), $D^{337}$-$E^{347}$ (■) and $F^{351}$-$K^{355}$ (▲) is shown at the left with a summary of the initial rate of deuterium exchange from 3-30 seconds at the right.

Figure 6A:
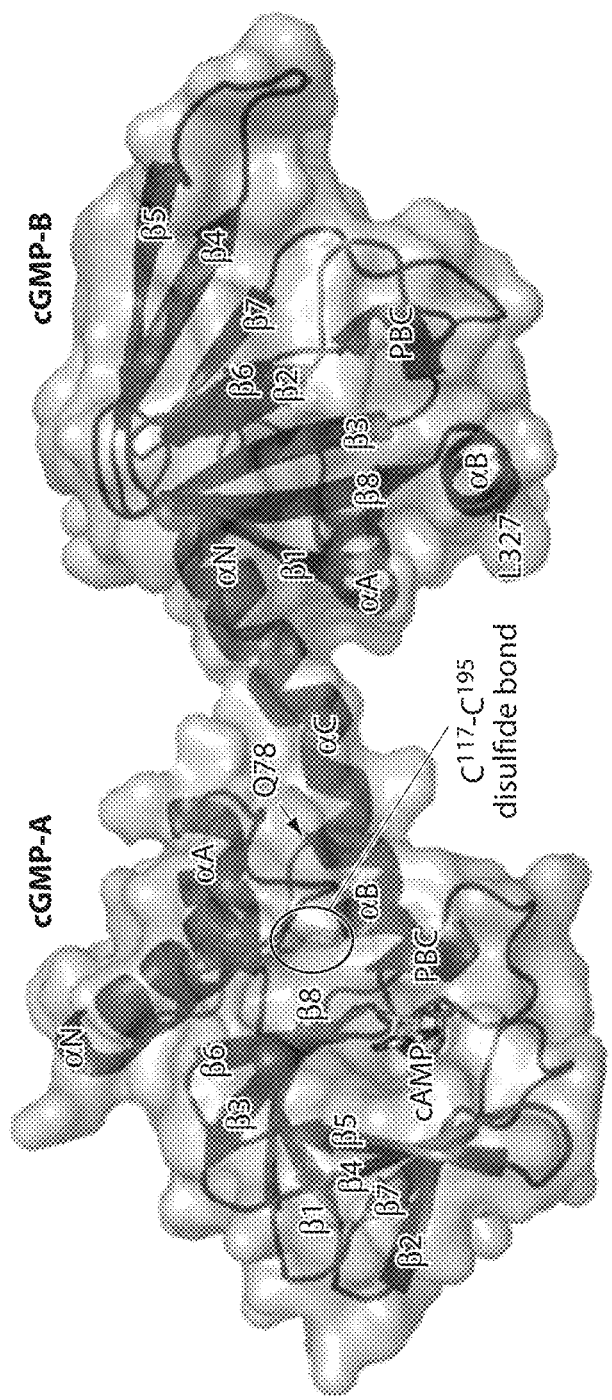
FIG. 6: Topology of the cGMP-Binding Domains (A) Overall fold of the tandem cGMP binding domains shown as cartoon representation with secondary structural elements labeled (switch helix not shown). (B) Overlay of cGMP-A (dark gray) with cGMP-B (white). RMSD=1.214 for Ca molecules. PBC from cGMP-A is labeled as PBC, $C^{117}$-$C^{195}$ disulfide bond is circled and labeled.
Figure 6B:
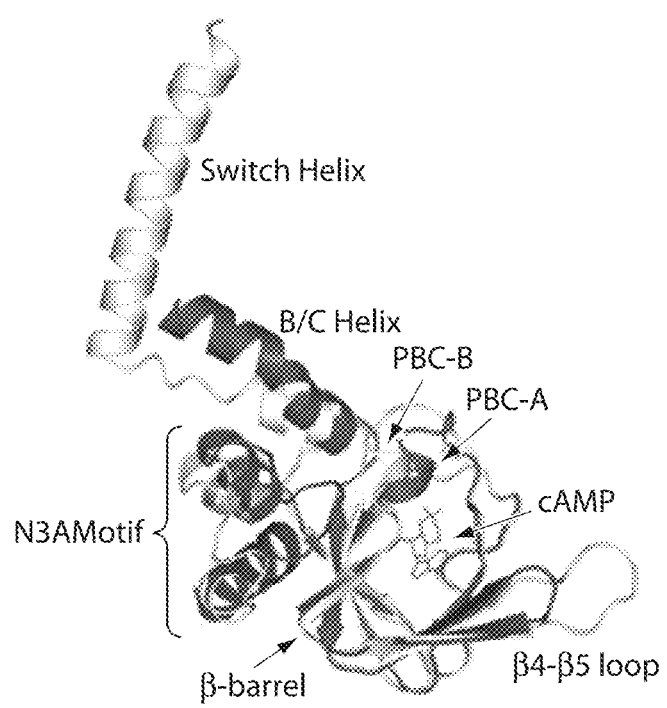

Both cGMP-binding sites exhibit classic features of the conserved CNB fold (FIG. 6A). A rigid eight-stranded β-barrel sandwiches the phosphate binding cassette (PBC) between β strands 6 and 7 which serves as a docking site for cNTs. The β-barrel itself is flanked at the N terminus by the αN helix, the 310 loop, and the αA helix (collectively termed the N3A motif) and C-terminally by the αB/αC helix. Surprisingly, the two CNB domains presented in this structure have been captured in different conformational states as is evident when comparing helical elements between A- and B-domains (FIG. 6B). Superimposition of the two cGMP-binding yields an rmsd of 1.124. While the β-barrels superimpose well, there is variance in the helical subdomains. FIG. 6 shows the topology of the cGMP-Binding Domains. The overall fold of the tandem cGMP binding domains is shown as a cartoon representation with secondary structural elements labeled (switch helix not shown).

The two cGMP-binding sites are separated by an elongated B/C helix at the end of the A-domain (FIG. 6A). This creates a dumbbell-like topology between the two CNB domains and resembles the conformation adopted by regulatory subunits of PKA when bound to the catalytic subunits in the holoenzyme conformation (Kim et al., 2007; Wu et al., 2007). A kink in the C helix in the middle of this cleft is a likely point at which the two CNB domains undergo cGMP-mediated structural rearrangements. Residues in this kink are clearly solvent exposed (FIG. 5B; FIG. 12A) and proteolysis at $Arg^{202}$ readily occurs in the absence of cGMP (Chu et al., 1997; Scholten et al., 2007). Incubation with cGMP induces conformational changes that prevent such proteolysis. Furthermore, cGMP binding increases solvent protection in this region (Alverdi et al., 2008) further suggesting that the A-domain C helix may be the center of cGMP induced conformational changes in the regulatory domain.

The extended conformation of $PKG^{78-355}$ does not appear to allow direct communication between the A- and B-domains. This suggests that the structural determinants mediating cooperative binding of cGMP are not contributed by the core of the regulatory domain. In support of this finding, previous studies have demonstrated a loss of cooperativity upon deletion of regions outside the cGMP-binding domains (Dostmann et al., 1996; Heil et al., 1987). Moreover, in PKA holoenzyme structures of both type Ia (Kim et al., 2007) and IIα (Wu et al., 2007) the catalytic subunit docks to the cleft created by the extended topology of the CNB domains in the regulatory subunits. Residue Gln78, just C-terminal to the AI domain in PKG, is positioned in the center of the two cGMP-binding sites (FIG. 5B), which is where the N terminus of PKG interacts with the catalytic core of the enzyme via the AI domain (Heil et al., 1987; Hofmann et al., 2009). While the precise docking mechanism may differ in the PKG holoenzyme, the catalytic domain is likely to sit in this cleft and participate in crosstalk between the two cGMP-binding sites similar to the architectural arrangements observed in PKA.

Example 2

The A-Domain is cAMP Bound

The docking of cNTs to a CNB domain is made possible by the conserved and mobile motif of the PBC (FIG. 7A) (Diller et al., 2001; McKay et al., 1982; Su et al., 1995). This short, 14 residue helix-turn contains residues that coordinate the ribose-phosphate moiety and allows for the preferential binding of cAMP versus cGMP. Invariantly, all CNB domains from cNT-regulated protein kinases have a Glu in the 3 position and an Arg in the 12 position, which hydrogen bonds with the 2'OH and equatorial oxygen, respectively. Unique to PKG is a Thr or Ser in the 13 position of the PBC, which has been predicted to provide specificity for cGMP by providing a hydrogen bond potential with both the 2-$NH_2$ and apical oxygen of cGMP (Shabb and Corbin, 1992; Weber et al., 1989). PKA contains an Ala in the 13-position and mutation of this residue to a Thr produces a PKA mutant that no longer discriminates between cAMP and cGMP (Shabb et al., 1990).

Figure 7C:
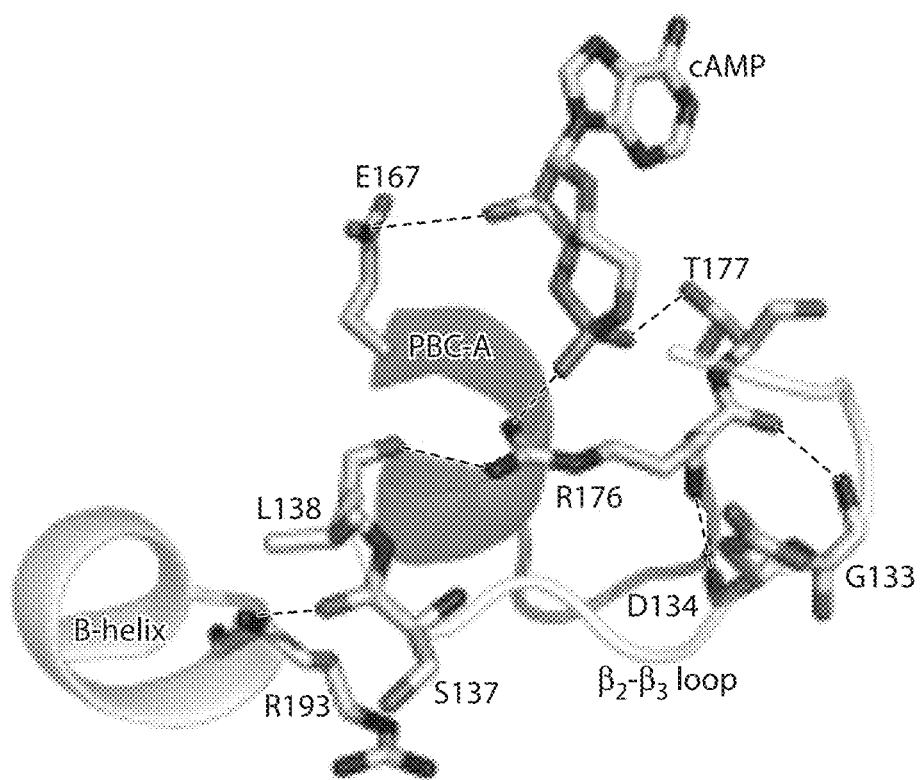
FIG. 7 Features of the A-Domain (A) Sequence alignment for PBCs from PKA and PKG Iα isoforms. Threonine residues in the 13 position of PKG PBCs are highlighted by a box. SEQ ID NOs: 11-30 from left to right and top to bottom. (B) Composite omit map generated for the cNT binding sites of both A-domains contoured to 1.5 s. syn-cAMP is modeled into the positive density. (C) Specific interactions between the sugar-phosphate moiety of cAMP and residues from the PBC. The 2'-hydroxyl hydrogen bonds with $Glu^{167}$, the equatorial oxygen of the phosphate group interacts with $Arg^{176}$, and the apical oxygen contacts both the side-chain hydroxyl and backbone amino groups of $Thr^{177}$. The backbone carbonyl of $Leu^{138}$ bridges communication from the guanidinium group of $Arg^{176}$ through the β2-β3 loop to $Arg^{193}$ in the B helix. (D) A hydrophobic face accommodates the solvent-exposed nucleobase. (E) Schematic of cNT binding to the A-domain of PKG $Iα^{78-355}$ with cGMP modeled in place of the observed cAMP. Specific hydrogen bond contacts are shown as dotted lines. Interactions coming from backbone amide (□) and carbonyl (○) are highlighted, whereas side-chain interactions are shown from the center of the circled residue. Hydrophobic interactions with the cNT are shown as boxed residues.

FIG. 7 shows the features of the A-Domain. For instance the sequence alignment for PBCs from PKA and PHG Iα isoforms is shown in 7A. Threonine residues in the 13 position of PKG PBCs are highlighted by a box. A composite omit map generated for the cNT binding sites of both A-domains contoured to 1.5 s. syn-cAMP is modeled into the positive density as shown in FIG. 7B. Specific interactions between the sugar-phosphate moiety of cAMP and residues from the PBC are shown in FIG. 7C. The 2'-hydroxyl hydrogen bonds with $Glu^{167}$, the equatorial oxygen of the phosphate group interacts with $Arg^{176}$, and the apical oxygen contacts both the side-chain hydroxyl and backbone amino groups of $Thr^{177}$. The backbone carbonyl of $Leu^{138}$ bridges communication from the guanidinium group of Arg176 through the β3-β3 loop to $Arg^{193}$ in the B helix. A hydrophobic face accommodates the solvent-exposed nucleobase, as shown in 7D. A schematic of cNT binding to the A-domain of PKG $Iα^{78-355}$ with cGMP modeled in place of the observed cAMP is shown in 7E. Specific hydrogen bond contacts are shown as dotted lines. Interactions coming from backbone amide (□) and carbonyl (o) are highlighted, whereas side-chain interactions are shown from the center of the circled residue. Hydrophobic interactions with the cNT are shown as boxed residues.

To assess the occupancy of PBCs in the $PKG^{78-355}$ structure, initial phases from the molecular replacement solution were used to generate a simulated annealing composite omit map. In order to minimize model bias, side chains for the invariant Glu, Arg, and Thr residues were omitted in each PBC. A strong positive peak was observed in the A-domain which resembled a cyclic-30,50-nucleotide monophosphate containing a purine moiety in the syn configuration (FIG. 7B), while the B-domain appeared cNT-free. While electron density at the 2'OH of the ribose and the 6 position of the purine was evident, we could not attribute the 6 position density to being either a keto/enol or amino group. However, there was no density extending from the 2 position where the 2-amino group of cGMP should reside. This was a clear indication that the cNT occupying the A-domain was syn-oriented cAMP. HPLC analysis and UV-spectroscopy confirmed the presence of cAMP and the absence of cGMP (see methods).

The primary interactions made with the cyclic nucleotide come from residues buried within the PBC. Specific contacts are made by $Glu^{167}$, $Arg^{176}$, and $Thr^{177}$ (FIG. 7C). $Glu^{167}$ forms a hydrogen bond with the 2'OH of the ribose and $Arg^{176}$ docks the equatorial oxygen of the phosphate. $Thr^{177}$ hydrogen bonds with the apical oxygen of the phosphate group with both side-chain hydroxyl and backbone amino groups. Modeling of syn-oriented cGMP into the A-domain maintains these same contacts and shows that the 2-amino group is primed to interact with the $Thr^{177}$ side-chain hydroxyl. The Glu and Arg contacts are similar to those used by the cAMP-PKA interaction and the previously predicted interactions with $Thr^{177}$ are confirmed (Shabb et al., 1991; Weber et al., 1989). A schematic summary of these specific interactions with cGMP modeled into the A-domain is presented in FIG. 7E.

Figure 7D:
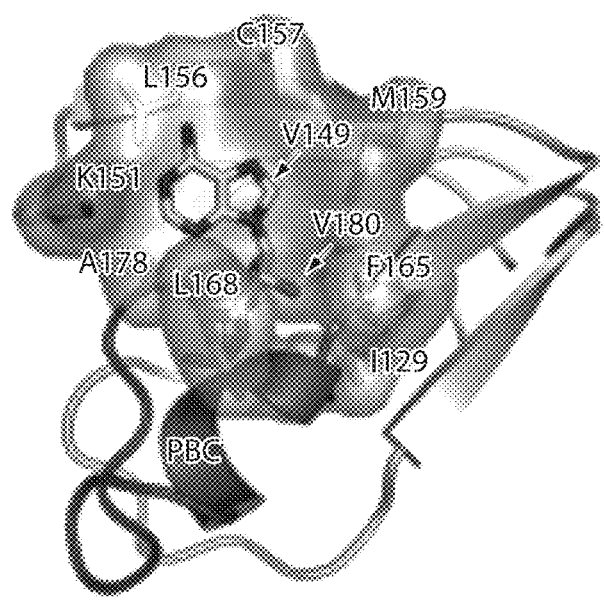
Figure 7E:
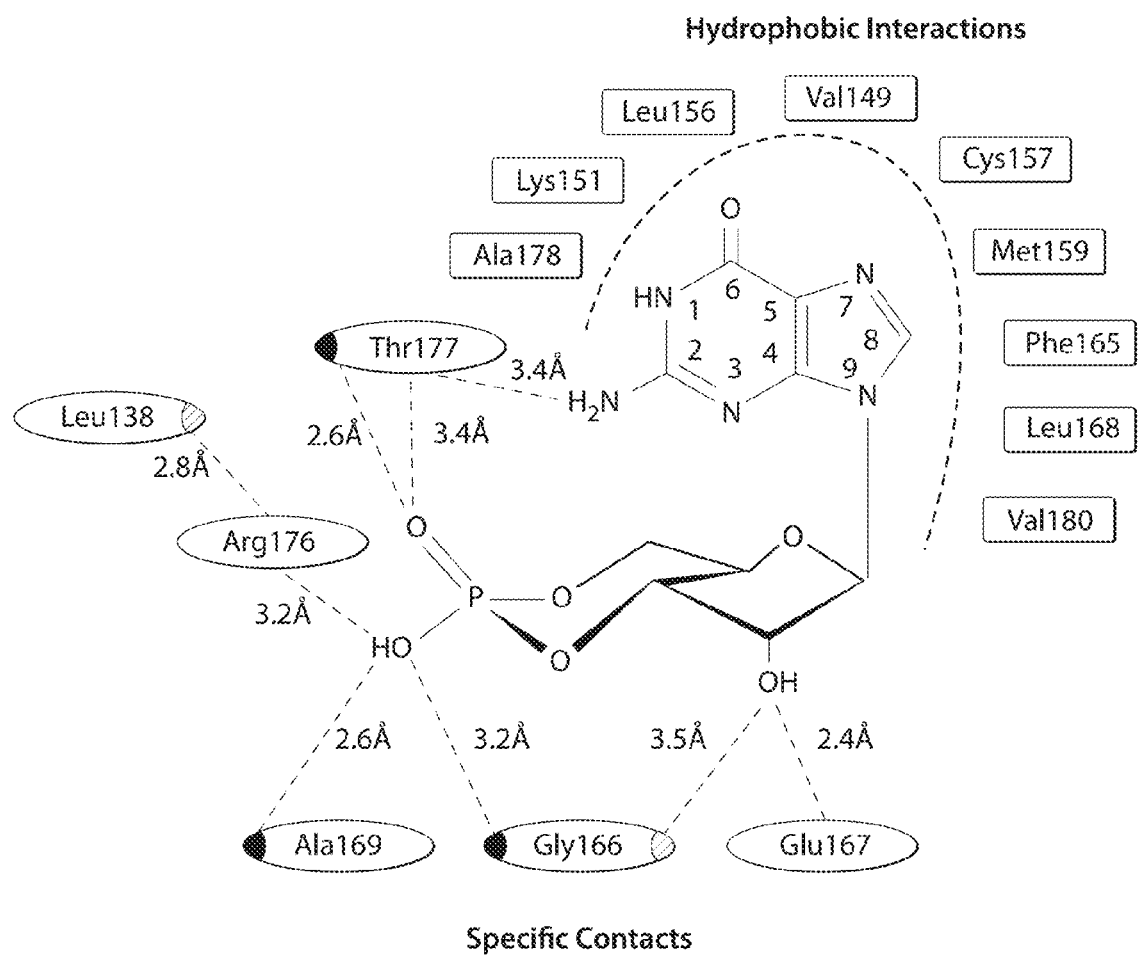

As has been described for other CNB domain structures, cNT docking to the PBC is stabilized by a capping mechanism that sandwiches the nucleotide base between hydrophobic surface on the b-barrel, and a hydrophobic cap that moves into place upon cNT-induced structural rearrangements of the protein (Berman et al., 2005; Das et al., 2007). In the PKG$^{78-355}$ structure, the backside of the adenine ring is flanked by an array of hydrophobic contacts with no obvious hydrogen bond donor or acceptor potentials (FIG. 7D). The identity of the specific capping residue is not disclosed, however, because the two CNB domains are in an extended, inactive conformation and capping occurs only after ligand-mediated conformational changes cause the two CNB domains to form a more compact structure.

A second shell of regulation is provided by the β2-β3 loop. In PKA this loop stabilizes the PBC arginine and provides allosteric communication of binding events in the PBC to the B helix. In the A-domain of PKG Iα, Arg$^{176}$ is coordinated by a number of conserved residues from the β2-β3 loop (FIG. 7C). A hydrophobic interaction is made with Ile$^{130}$, and the backbone carbonyl and amide of Arg$^{176}$ forms hydrogen bonds with the Gly$^{133}$ amide and Asp$^{134}$ carbonyl, respectively. Furthermore, the guanidinium group of Arg$^{176}$ interacts with the carbonyl of Leu$^{138}$. Communication between the β2-β3 loop and the B helix occurs via Arg$^{193}$. The backbone amide of Arg$^{193}$ is bridged by the carbonyl of Ser$^{137}$. This is where PKG differs from PKA. The equivalent to Ser$^{137}$ is Asp$^{170}$ in the PKA RIαA-domain which hydrogen bonds not only with the backbone amide of the Arg in the B helix, but also coordinates the guanidinium of the PBC Arg. In doing so, a direct link from the PBC to the B helix hinge is made via the β2-β3 loop. In contrast, the PKG A-domain does not utilize this same direct allosteric mechanism. This may be a critical divergence in how these two cNT-regulated protein kinases communicate binding events in their PBCs with the rest of the molecule.

Example 3

A Cys$^{117}$-Cys$^{195}$ Disulfide Bond Locks A and B Helices in the A-Domain

The presence of disulfide bonds in PHG Iα have been reported and an oxidation-induced mechanism of activation has been proposed as complementary mechanism to cyclic nucleotide mediated regulation of kinase activity (Burgoyne et al., 2007; Landgraf et al., 1991). PHG Iα contains 11 cysteine residues (Takio et al., 1984), 5 of which have been suggested to contribute to oxidation-induced activation. Cys$^{42}$, just C-terminal of the D/D domain forms an intermolecular disulfide bond with Cys$^{42}$ from the opposing protomer in the holoenzyme assembly (Burgoyne et al., 2007). It has been suggested that H2O2-induced oxidation of PHG Iα promotes kinase activation via a bridging of these two cysteines. Additionally, exposure of PHG Iα to divalent cations with positive redox potentials promotes enzyme activation via disulfide bond formation between Cys$^{117}$-Cys$^{195}$ and/or Cys$^{312}$-Cys$^{518}$ (Landgraf et al., 1991). It was unclear, however, whether Cys$^{117}$-Cys$^{195}$ or Cys$^{312}$-Cys$^{518}$ was exclusively responsible for the observed oxidation-induced activation. Despite the observations that cysteine oxidation can lead to cGMP-independent activation of PKG Iα, no molecular mechanism of activation has been proposed.

Figure 8A:
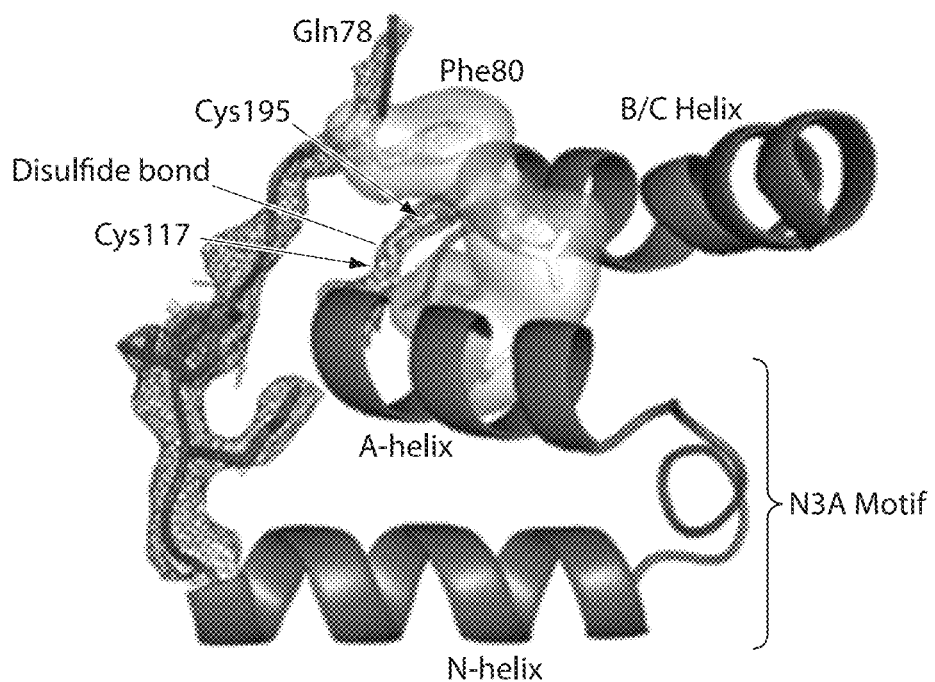
FIG. 8 Details of the $Cys^{117}$-$Cys^{195}$ Disulfide Bond (A) The disulfide bridge in the A-domain between $Cys^{117}$ and $Cys^{195}$ covalently links the A helix to the B helix. $2F_o$-$F_c$ electron density contoured to 1.6 s is shown for the loop preceding the N helix and the disulfide bond. (B) Side view of the hydrophobic sheath surrounding the disulfide bond.
Figure 8B:
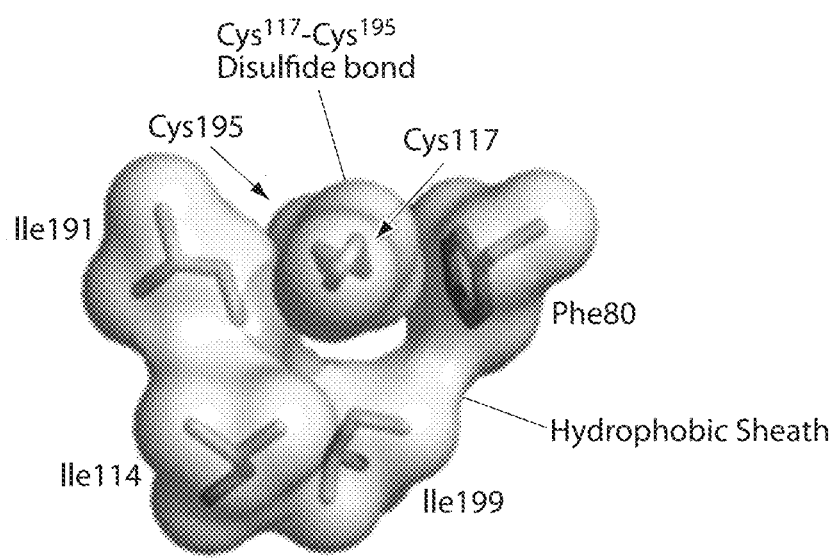

The PKG$^{78-355}$ structure reveals a disulfide bridge between Cys$^{117}$ in the A helix and Cys$^{195}$ at the start of the B helix (FIG. 8A). Residues immediately C-terminal of these two cysteines are solvent-exposed (FIG. 12A), while a hydrophobic sheath (Phe$^{80}$, Ile$^{114}$, Ile$^{191}$, and Ile$^{199}$) surrounds the disulfide bridge and provides solvent protection (FIG. 8B). In support of the oxidation-induced activation of PKG Iα previously observed (Landgraf et al., 1991), the recruitment of Phe$^{80}$ to the hydrophobic sheath provides a hypothesis as to how the enzyme might be activated in the absence of cGMP. The capping of Cys$^{117}$-Cys195 by Phe$^{80}$ serves to order the loop that precedes the N helix of the A-domain (FIG. 8A). As the AI domain resides just adjacent to Phe$^{80}$, autoinhibition of the kinase may be relieved through a movement of this loop to the hydrophobic sheath. The reorganization of this region upon oxidation of Cys$^{117}$-Cys$^{195}$ may disrupt the interaction between the AI and catalytic center thereby releasing the kinase from a state of autoinhibition. Furthermore, the sulfhydryl group of Cys$^{312}$ sits on β8 of the B-domain and points inward toward the center of the β-barrel (not shown). It seems unlikely that Cys$^{312}$ is capable of forming a disulfide bridge with Cys$^{518}$ from the activation loop in the catalytic domain. Our structure supports the Cys$^{117}$-Cys$^{195}$ disulfide bond as being involved in the metal-induced activation of PKG Iα.

FIG. 8 shows some details of the Cys$^{117}$-Cys$^{195}$ Disulfide Bond. The disulfide bridge in the A-domain between Cys$^{117}$ and Cys$^{195}$ covalently links the A helix to the B helix. $2F_o$-$F_c$ electron density contoured to 1.6 s is shown for the loop preceding the N helix and the disulfide bond.

Example 4

Mixed Configuration of the Two CNB Domains

The cNT-dependent structural dynamics of CNB domains are well established (Berman et al., 2005; Komev et al., 2008; Rehmann et al., 2007). While the β-barrel does not appear to undergo significant conformational changes upon cNT binding, the α-helical subdomain moves In and Out relative to the barrel (Table 2). Ligand association with the PBC initiates these structural changes as several residues make specific interactions with the nucleotide and close the PBC. This structural change is communicated through hydrophobic residues to the N3A motif and B/C helix. As a result, an extended B/C helix forms a hinge and closes inward toward the β-barrel. This rearrangement is accompanied by an outward shift of the N3A motif. In PKA, these cNT-induced conformational changes bring the two CNB domains closer together, which is then stabilized by the association of a hydrophobic capping residue with the nucleotide base. Although there is sequence and spatial variability as to the identity of the cap that secures the nucleotide base to the β-barrel, this allosteric mechanism is present in all CNB domain structures described to date.

TABLE 2

Summary of the Different Positions for Each Helical Component of CNB Domains from PKA RIα and the PKG$^{78-355}$ Structure

| CNB Domain | state | PBC | N3A Motif | B/C Helix |
|---|---|---|---|---|
| PKA RIα:Ca | apo | OPEN | IN | OUT |
| PKA RIα:cAMP | cNT bound | CLOSED | OUT | IN |
| PKG-A | Transition | CLOSED | IN | OUT |
| PKG-B | Transition | OPEN | OUT | OUT |

Figure 9A:
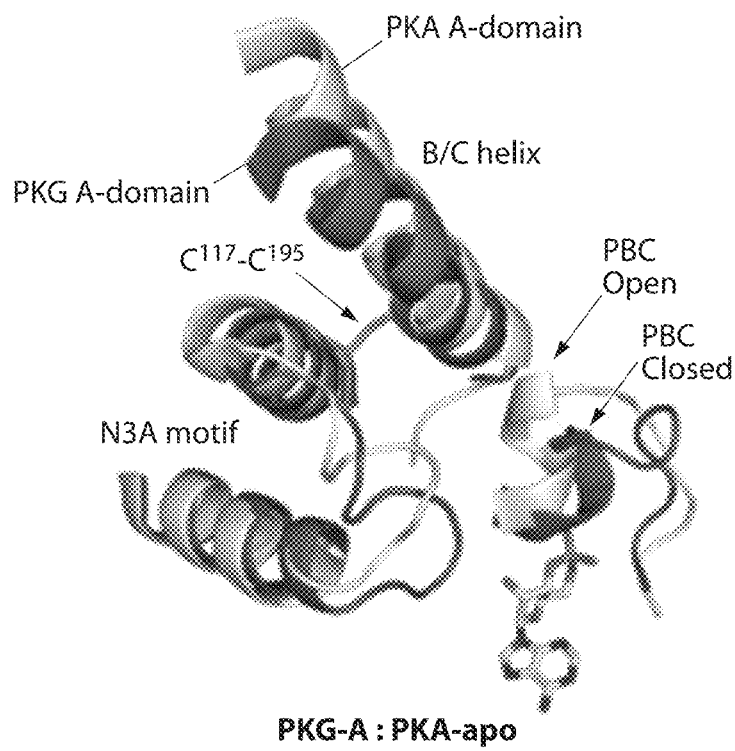
FIG. 9 Comparative Overlay of Helical Subdomains for PKG and PKA CNB Domains (A) Structural overlay of PKG A-domain (dark gray) with PKA A-domain (light gray) from the unliganded, holoenzyme structure (left, 2QCS) and the cAMP-bound form (right, 1RGS). (B) Structural overlay of PKG B-domain (dark gray) with PKA B-domain (light gray) from the unliganded, holoenzyme structure (left, 2QCS) and the cAMP-bound form (right, 1RGS).
Figure 9A:
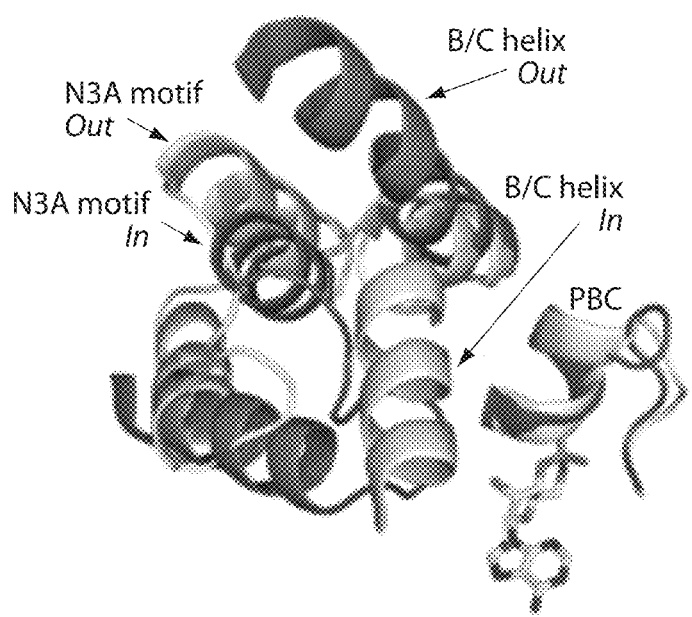
Figure 9B:
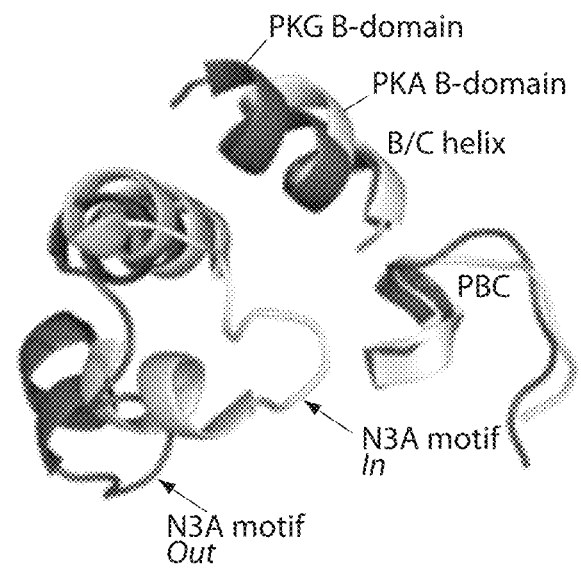
Figure 9B:
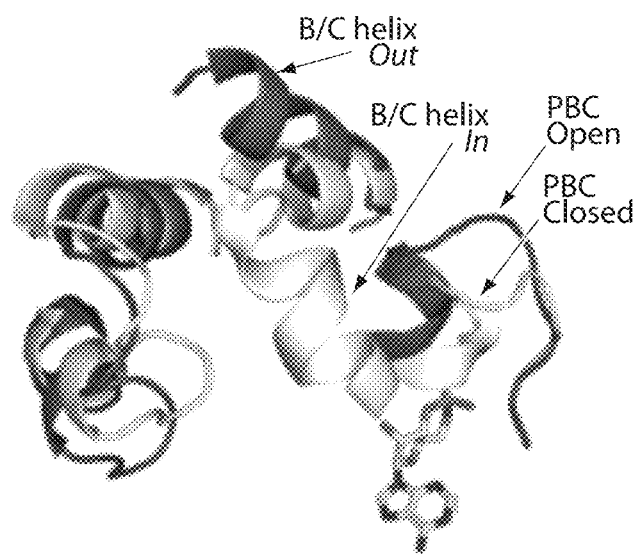

The two CNB domains presented here are in a mixed, hybrid configuration, with helical elements in both apo and cNT bound orientations (Table 2). As only the high affinity A-domain is cNT bound, the A-domain PBC is closed, relative to that of the B-domain (FIG. 6B). However, the subsequent conformational changes inherent to CNB domains are not observed. An overlay of the CNB domains from PKG and PKA indicate that the overall fold is conserved, but positional differences in the helical subdomain evince the hybrid nature of this PKG structure (FIGS. 9A and 9B). The B/C helix of the A-domain is clearly extended and the N3A motif is In, representative of a CNB domain in the apo, unliganded state rather than a cNT-bound conformation (Kornev et al., 2008; FIG. 9A). Despite the A-domain PBC being occupied by cAMP, allosteric communication of this binding event with the rest of the domain is severed. Interestingly, the $Cys^{117}$-$Cys^{195}$ disulfide bond provides a major structural determinant for this stable transition state. The covalent bridging of the A helix to the B helix prevents the B/C helix from closing upon cNT binding to the PBC. In turn, the N3A motif cannot move out from the b-barrel (FIG. 9A, arrow). This disulfide bond therefore uncouples communication of allosteric events in the A-domain from being transmitted to the B-domain.

The B-domain of this PKG structure is similarly locked in a hybrid conformation. This CNB domain is cNT free, thus the unbound PBC is Open and maintains an extended B/C helix (FIG. 9B). However, the N3A motif is also Out, an orientation reminiscent of a cNT-bound state (Kornev et al., 2008). The B-domain N3A motif is stabilized in the Out position by a set of hydrophobic residues originating from the C-terminal end of the SW in the other molecule in the asymmetric unit. The two symmetry mates are related by noncrystallographic symmetry and this interaction promotes a previously uncharacterized docking interface between PHG Iα protomers, which is described in detail below.

Example 5

$PKG^{78-355}$ Protomers Interact Via their Switch Helices

Figure 10A:
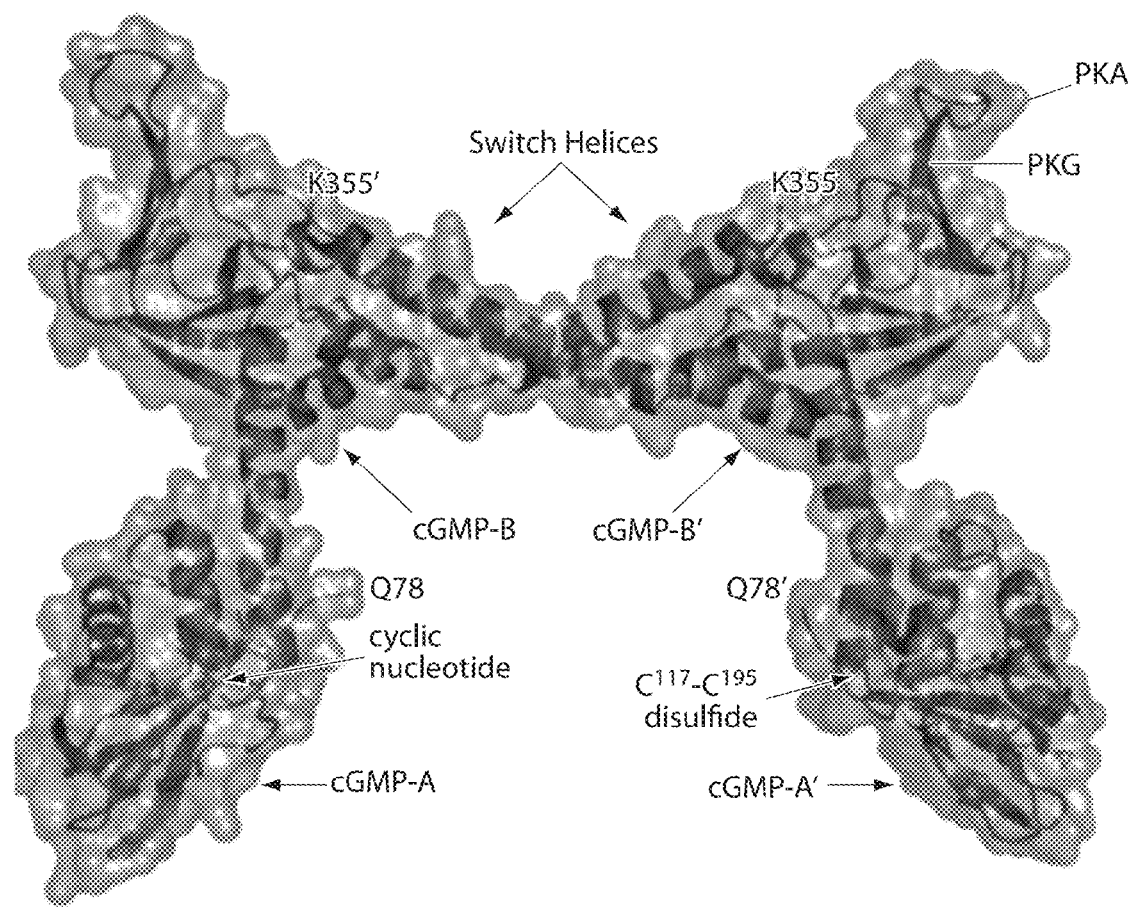
FIG. 10 Dimeric View of PKG$^{78-355}$ Protomers (A) Ribbon diagram of two PKG$^{78-355}$ protomers as observed in the asymmetric unit. (B) "Front" and Top" views of surface representation of the PKG$^{78-355}$ dimer to illustrate the crossing of switch helices.
Figure 10B:
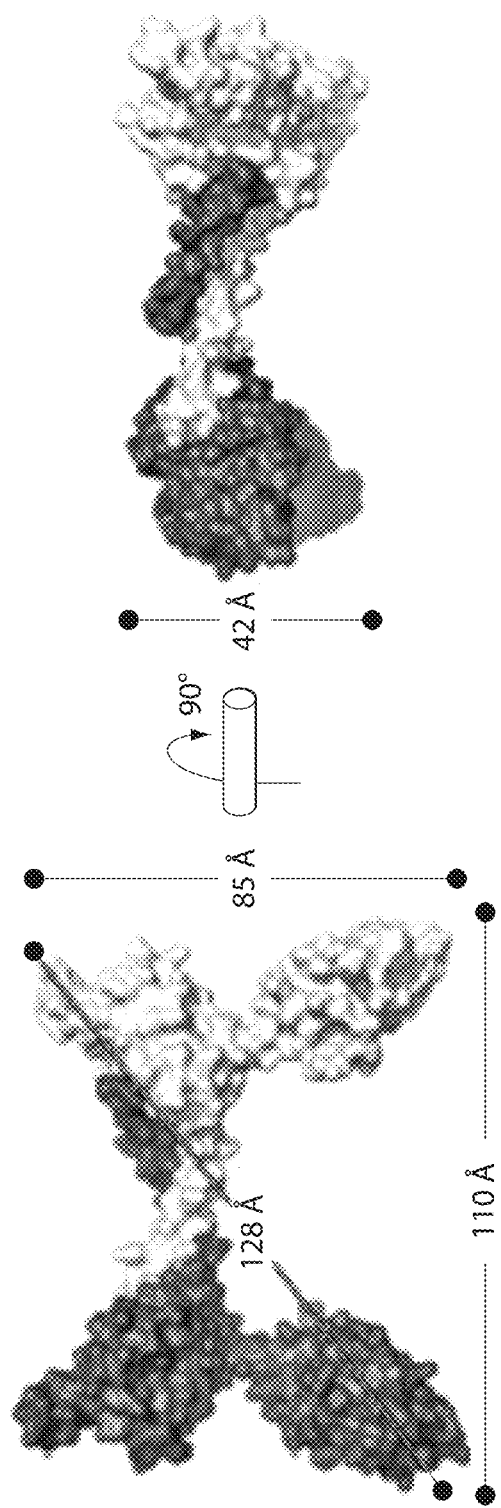
Figure 13A:
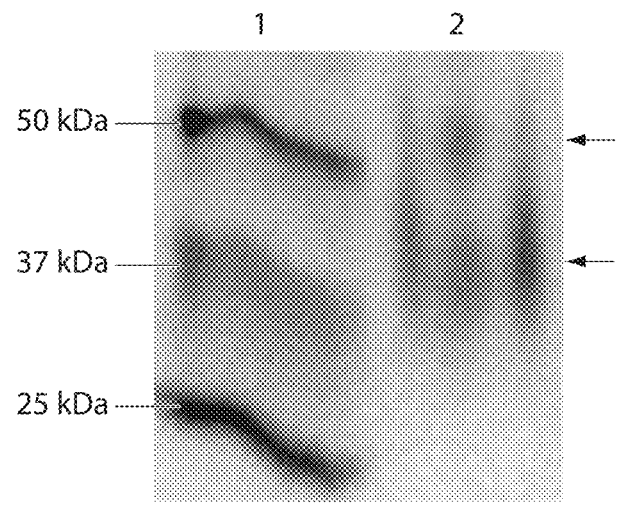
FIG. 13 Native PAGE analysis of PKG$^{78-355}$. (A) 5 μg of purified PKG$^{78-355}$ in solution exhibited two distinct populations consistent with monomeric and dimeric forms of the protein (lane 2). (B) PKG$^{78-355}$ taken from crystals dissolved in Buffer A (see methods) migrated corresponding to the dimer. Each gel was 9.5% acrylamide lacking SDS. Gels were run at constant voltage (200V) on ice for 2 hours.
Figure 13B:
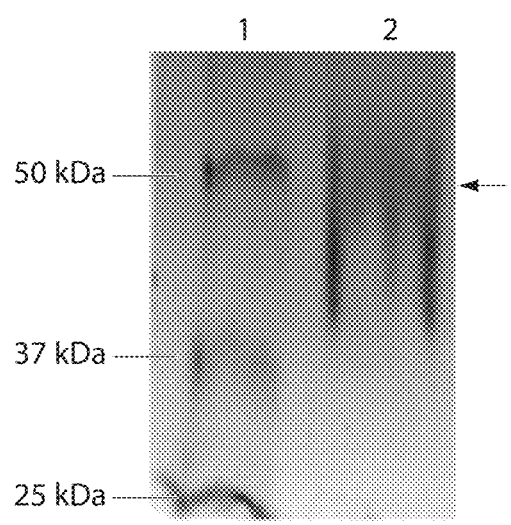

Remarkably, the $PKG^{78-355}$ crystal structure forms a symmetry related dimer through the formation of an interface between the SW and the opposing B-domain (FIGS. 10A and 10B). It is well established that PKG assembles into parallel homodimers, an assembly mediated by leucine zipper motifs at the immediate N termini. The structure presented here provides the first evidence for intermolecular communication at sites distal to the classical N-terminal D/D domain. The SW extends from the B-domain and residues at the C terminus of each SW interact with an open hydrophobic network in the B-domain of the opposing protomer (FIGS. 11A and 11B). Hydrophobic "knobs" at the end of the SW (residues 350-354) stabilize the open N3A motif in the B-domain of the neighboring protomer. Side chains from $Phe^{350}$, $Phe^{351}$, and $Leu^{354}$ fill the void created by an extensive hydrophobic "nest" (FIGS. 11A and 11B). The eight residues that comprise the nest ($Phe^{221}$, $Leu^{224}$, $Leu^{232}$, $Trp^{228}$, $Gln^{295}$, $Phe^{320}$, $Ile324$, $Leu^{327}$) are noncontiguous and recruited from the entire B-domain (FIG. 12A). This knob-nest interface is further strengthened by $Asn^{353}$, the only polar residue at the end of the SW, which forms a hydrogen bond with the backbone carbonyl of $Thr^{220}$ in the 310 loop of the B-domain (FIGS. 11A and 11B). Formation of this dimeric assembly protects 2740 Å 2 of surface area, and has a free energy (DG) of 15.8 kcal/mol required for dissociation, an indication that this arrangement is thermodynamically stable in solution. Native PAGE analysis of $PKG^{78-355}$ in solution displays a small population of dimeric protein (FIG. 13A). Similarly, the migration of crystalline $PKG^{78-355}$ is consistent with a dimer (FIG. 13B).

Our initial DxMS studies on $PKG^{78-355}$ offered further validation of the significance of this knob-nest interface. Analysis of peptide fragments from the SW indicated that the C-terminal residues containing the hydrophobic knobs and $Asn^{353}$ had a slower rate of deuterium exchange compared with residues in the more solvent-exposed region of this helix. This finding suggested that the very C terminus of the SW is protected in solution and that the knob-nest interaction may serve as the focal point of interchain communication between PKG protomers. Interestingly, the knob residues appear to be unique to PKG I isoforms, as PKG II has a large amino acid insertion at the site of the SW (see sequence alignment, FIG. 12A). However, hydrophobic residues at the equivalent nest positions are conserved in both PKG I and II isoforms.

Example 6

Figure 11C:
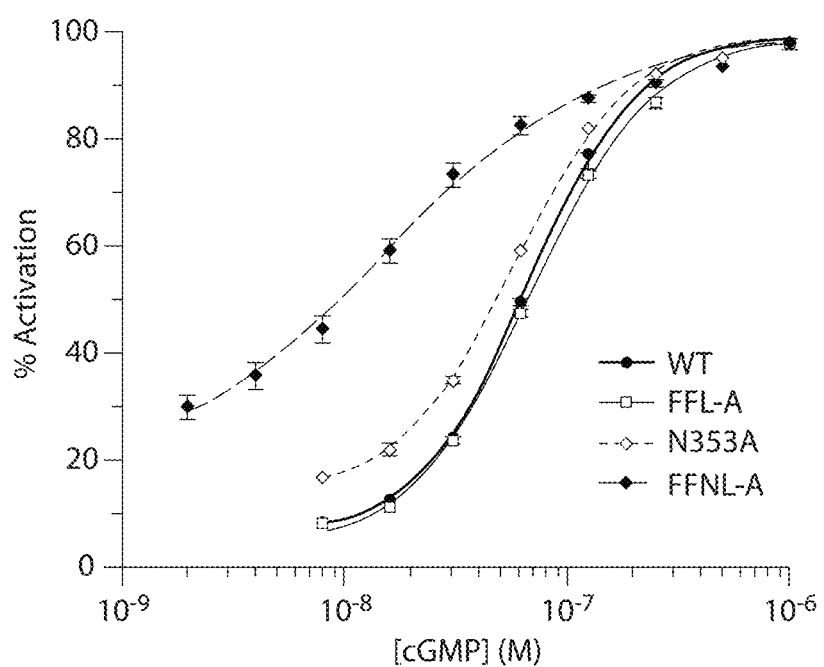

Mutational Disruption of the Knob-Nest Interface in Full-Length PHG Iα Decreases the Activation Constant and Suggests a Tethering Mechanism for the Catalytic Domain The functional relevance of the knob-nest interface was probed by Alanine scanning mutagenesis of the SW knob residues in full-length PHG Iα containing both the N-terminal D/D and the catalytic domains. Extracts from HEK293 cells expressing wild-type and mutant PHG Iα were examined for phosphoryl transfer activity. Removal of the specific hydrogen bond provided by $Asn^{353}$ ($N^{353}A$) resulted in a significantly decreased activation constant (FIG. 11C and Table 3). The entire knob nest interface was disrupted by a quadruple mutation wherein all hydrophobic knob residues in addition to the specific $Asn^{353}$ were substituted for alanine ($F^{350}A$, $F^{351}A$, $N^{353}A$, $L^{354}A$). Neutralization of these interactions further reduced the activation constant greater than 4-fold (FIG. 11C and Table 3). Additionally, this mutant displayed a loss of cooperativity (nH). While we were unable to calculate absolute basal and Vmax values, the relative changes in KA, combined with the observed decrease in Hill coefficient, illustrates the importance of the knob-nest interface in maintaining the kinetic fidelity of PKG Iα. In the context of full-length PKG Iα, the SW seems to act as a tether for the catalytic domain, disruption of which causes the kinase to be more easily activated.

TABLE 3

Summary of Kinetic Analysis from FIG. 7C

| Mutation | $K_A$ (nM) | $n_H$ | Fold Activation |
|---|---|---|---|
| WT (n = 12) | 67 ± 2 | 1.7 ± 0.09 | 11.0 |
| $F^{350}A/F^{351}A/L^{354}A$ (n = 4) | 70 ± 5 | 1.6 ± 0.06 | 12.3 |
| $N^{353}A$ (n = 9) | 57 ± 1 | 1.7 ± 0.06 | 5.9 |
| $F^{350}A/F^{351}A/L^{354}A$ (n = 10) | 15.3 ± 1.7 | 0.8 ± 0.09 | 3.1 |

Activation constants ($K_A$) and Hill coefficients ($n_H$) are presented for WT PKG Iα and SW knob mutants. A statistically significant difference in $K_A$ was noted for both the $N^{353}A$ and $F^{350}A/F^{351}A/N^{353}A/L^{354}A$ mutants (p < 0.001) compared with WT PKG Iα.

REFERENCES

Aitken, A., Hemmings, B. A., and Hofmann, F. (1984). Identification of the residues on cyclic GMP-dependent protein kinase that are autophosphorylated in the presence of cyclic AMP and cyclic GMP. Biochim Biophys. Acta 790, 219-225.

Alverdi, V., Mazon, H., Versluis, C., Hemrika, W., Esposito, G., van den Heuvel, R., Scholten, A., and Heck, A. J. (2008). cGMP-binding prepares PKG for substrate binding by disclosing the C-terminal domain. J. Mol. Biol. 375, 1380-1393.

Berman, H. M., Ten Eyck, L. F., Goodsell, D. S., Haste, N. M., Kornev, A., and Taylor, S. S. (2005). The cAMP binding domain: an ancient signaling module. Proc. Natl. Acad. Sci. USA 102, 45-50.

Bian, K. and F. Murad, *Nitric oxide signaling in vascular biology*. Journal of the American Society of Hypertension: JASH, 2007. 1(1): p. 17-29. Boettcher, A. J., Wu, J., Kim, C., Yang, J., Bruystens, J., Cheung, N., Pennypacker, J. K., Blumenthal, D. A., Kornev, A. P., and Taylor, S. S. (2011). Realizing the allosteric potential of the tetrameric protein kinase A RIa holoenzyme. Structure 19, 265-276.

Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., et al. (1998). Crystallography & NMR system: A new software suite for macromolecular structure determination. Acta Crystallogr. D Biol. Crystallogr. 54, 905-921.

Bryan, N. S., K. Bian, and F. Murad, *Discovery of the nitric oxide signaling pathway and targets for drug development*. Frontiers in bioscience: a journal and virtual library, 2009. 14: p. 1-18.

Burgoyne, J. R., Madhani, M., Cuello, F., Charles, R. L., Brennan, J. P., Schroder, E., Browning, D. D., and Eaton, P. (2007). Cysteine redox sensor in PKGIa enables oxidant-induced activation. Science 317, 1393-1397.

Burns-Hamuro, L. L., Hamuro, Y., Kim, J. S., Sigala, P., Fayos, R., Stranz, D. D., Jennings, P. A., Taylor, S. S., and Woods, V. L., Jr. (2005). Distinct interaction modes of an AKAP bound to two regulatory subunit isoforms of protein kinase A revealed by amide hydrogen/deuterium exchange. Protein Sci. 14, 2982-2992.

Butt, E., D. Pohler, H. G. Genieser, J. P. Huggins, and B. Bucher, *Inhibition of cyclic GMP-dependent protein kinase-mediated effects by (Rp)-8-bromo-PET-cyclic GMPS*. British journal of pharmacology, 1995. 116(8): p. 3110-6

Chu, D. M., Corbin, J. D., Grimes, K. A., and Francis, S. H. (1997). Activation by cyclic GMP binding causes an apparent conformational change in cGMP dependent protein kinase. J. Biol. Chem. 272, 31922-31928.

Das, R., Esposito, V., Abu-Abed, M., Anand, G. S., Taylor, S. S., and Melacini, G. (2007). cAMP activation of PKA defines an ancient signaling mechanism. Proc. Natl. Acad. Sci. USA 104, 93-98.

Diller, T. C., Madhusudan, Xuong, N. H., and Taylor, S. S. (2001). Molecular basis for regulatory subunit diversity in cAMP-dependent protein kinase: crystal structure of the type II beta regulatory subunit. Structure 9, 73-82.

Dostmann, W. R., *(RP)-cAMPS inhibits the cAMP-dependent protein kinase by blocking the cAMP-induced conformational transition*. FEBS letters, 1995. 375(3): p. 231-4.

Dostmann, W. R., Koep, N., and Endres, R. (1996). The catalytic domain of the cGMP-dependent protein kinase Ialpha modulates the cGMP-binding characteristics of its regulatory domain. FEBS Lett. 398, 206-210.

Dostmann, W. R., Nickl, C., Thiel, S., Tsigelny, I., Frank, R., and Tegge, W. J. (1999). Delineation of selective cyclic GMP-dependent protein kinase Ialpha substrate and inhibitor peptides based on combinatorial peptide libraries on paper. Pharmacol. Ther. 82, 373-387.

Dostmann, W. R. and S. S. Taylor, *Identifying the molecular switches that determine whether (Rp)-cAMPS functions as an antagonist or an agonist in the activation of cAMP-dependent protein kinase I. Biochemistry*, 1991. 30(35): p. 8710-6.

Dostmann, W. R., S. S. Taylor, H. G. Genieser, B. Jastorff, S. O. Doskeland, and D. Ogreid, *Probing the cyclic nucleotide binding sites of cAMP-dependent protein kinases I and II with analogs of adenosine 3',5'-cyclic phosphorothioates*. The Journal of biological chemistry, 1990. 265 (18): p. 10484-91.

Emsley, P., Lohkamp, B., Scott, W. G., and Cowtan, K. (2010). Features and development of Coot. Acta Crystallogr. D Biol. Crystallogr. 66, 486-501.

Feil, R., Bigl, M., Ruth, P., and Hofmann, F. (1993). Expression of cGMPdependent protein kinase in *Escherichia coli*. Mol. Cell. Biochem. 127-128, 71-80.

Francis, S. H. and J. D. Corbin, *Cyclic Nucleotide-Dependent Protein Kinases: Intracellular Receptors for cAMP and cGMP Action*. Critical Reviews in Clinical Laboratory Sciences, 1999. 36(4): p. 275-328.

Gill, G. N., and Garren, L. D. (1971). Role of the receptor in the mechanism of action of adenosine 30:50-cyclic monophosphate. Proc. Natl. Acad. Sci. USA 68, 786-790.

Gill, G. N., Walton, G. M., and Sperry, P. J. (1977). Guanosine 30:50-monophosphate-dependent protein kinase from bovine lung. Subunit structure and characterization of the purified enzyme. J. Biol. Chem. 252, 6443-6449.

Hamuro, Y., Anand, G. S., Kim, J. S., Juliano, C., Stranz, D. D., Taylor, S. S., and Woods, V. L., Jr. (2004). Mapping intersubunit interactions of the regulatory subunit (RIalpha) in the type I holoenzyme of protein kinase A by amide hydrogen/deuterium exchange mass spectrometry (DXMS). J. Mol. Biol. 340, 1185-1196.

Heil, W. G., Landgraf, W., and Hofmann, F. (1987). A catalytically active fragment of cGMP-dependent protein kinase. Occupation of its cGMP-binding sites does not affect its phosphotransferase activity. Eur. J. Biochem. 168, 117-121.

Hofmann, F., Bernhard, D., Lukowski, R., and Weinmeister, P. (2009). cGMP regulated protein kinases (cGK). Handb Exp Pharmacol, 137-162.

Kemp-Harper, B. and H. H. Schmidt, *cGMP in the vasculature*. Handbook of experimental pharmacology, 2009 (191): p. 447-67.

Kim, C., Cheng, C. Y., Saldanha, S. A., and Taylor, S. S. (2007). PKA-I holoenzyme structure reveals a mechanism for cAMP-dependent activation. Cell 130, 1032-1043.

Kleppisch, T. and R. Feil, *cGMP signalling in the mammalian brain: role in synaptic plasticity and behaviour*. Handbook of experimental pharmacology, 2009 (191): p. 549-79.

Kornev, A. P., Taylor, S. S., and Ten Eyck, L. F. (2008). A generalized allosteric mechanism for cis-regulated cyclic nucleotide binding domains. PLoS Comput. Biol. 4, e1000056.

Kots, A. Y., K. Bian, and F. Murad, *Nitric oxide and cyclic GMP signaling pathway as a focus for drug* development. Current medicinal chemistry, 2011. 18(22): p. 3299-305.

Krissinel, E., and Henrick, K. (2007). Inference of macromolecular assemblies from crystalline state. J. Mol. Biol. 372, 774-797.

Kuhn, M., *Molecular physiology of natriuretic peptide signalling*. Basic research in cardiology, 2004. 99(2): p. 76-82.

Landgraf, W., Regulla, S., Meyer, H. E., and Hofmann, F. (1991). Oxidation of cysteines activates cGMP-dependent protein kinase. J. Biol. Chem. 266, 16305-16311.

Leonard, T. A., Ro'_zycki, B., Saidi, L. F., Hummer, G., and Hurley, J. H. (2011). Crystal structure and allosteric activation of protein kinase C bII. Cell 144, 55-66.

McCoy, A. J., Grosse-Kunstleve, R. W., Adams, P. D., Winn, M. D., Storoni, L. C., and Read, R. J. (2007). Phaser crystallographic software. J. Appl. Cryst. 40, 658-674.

McDonald, L. J. and F. Murad, *Nitric oxide and cGMP signaling.* Adv Pharmacol, 1995. 34: p. 263-75.

McKay, D. B., Weber, I. T., and Steitz, T. A. (1982). Structure of catabolite gene activator protein at 2.9-A resolution. Incorporation of amino acid sequence and interactions with cyclic AMP. J. Biol. Chem. 257, 9518-9524.

Minor, Z. O. W., ed. (1997). Processing of X-ray Diffraction Data Collected in Oscillation Mode, part A edn (New York: Academic Press).

Ogreid, D., W. Dostmann, H. G. Genieser, P. Niemann, S. O. Doskeland, and B. Jastorff, *(Rp)- and (Sp)-8-piperidinoadenosine 3',5'-(cyclic)thiophosphates discriminate completely between site A and B of the regulatory subunits of cAMP-dependent protein kinase type I and II.* European journal of biochemistry/FEBS, 1994. 221(3): p. 1089-94.

Osborne, B. W., et al., *Crystal structure of cGMP-dependent protein kinase reveals novel site of interchain communication.* Structure, 2011. 19(9): p. 1317-27.

Pantazatos, D., Kim, J. S., Klock, H. E., Stevens, R. C., Wilson, I. A., Lesley, S. A., and Woods, V. L., Jr. (2004). Rapid refinement of crystallographic protein construct definition employing enhanced hydrogen/deuterium exchange MS. Proc. Natl. Acad. Sci. USA 101, 751-756.

Pfeifer, A., Ruth, P., Dostmann, W., Sausbier, M., Klatt, P., and Hofmann, F. (1999). Structure and function of cGMP-dependent protein kinases. Rev. Physiol. Biochem. Pharmacol. 135, 105-149.

Rehmann, H., Wittinghofer, A., and Bos, J. L. (2007). Capturing cyclic nucleotides in action: snapshots from crystallographic studies. Nat. Rev. Mol. Cell Biol. 8, 63-73.

Roger, V. L., et al., *Heart disease and stroke statistics—2011 update: a report from the American Heart Association.* Circulation, 2011. 123(4): p. e18-e209.

Roussel, A., and Cambillau, C. (1991). Silicon Graphics, Inc (CA: Mountain View).

Sandner, P., D. Neuser, and E. Bischoff, *Erectile dysfunction and lower urinary tract.* Handbook of experimental pharmacology, 2009 (191): p. 507-31.

Schlossmann, J. and F. Hofmann, *cGMP-dependent protein kinases in drug discovery.* Drug discovery today, 2005. 10(9): p. 627-34.

Scholten, A., Fuss, H., Heck, A. J., and Dostmann, W. R. (2007). The hinge region operates as a stability switch in cGMP-dependent protein kinase I alpha. FEBS J. 274, 2274-2286.

Shabb, J. B., Buzzeo, B. D., Ng, L., and Corbin, J. D. (1991). Mutating protein kinase cAMP-binding sites into cGMP-binding sites. Mechanism of cGMP selectivity. J. Biol. Chem. 266, 24320-24326.

Shabb, J. B., and Corbin, J. D. (1992). Cyclic nucleotide-binding domains in proteins having diverse functions. J. Biol. Chem. 267, 5723-5726.

Shabb, J. B., Ng, L., and Corbin, J. D. (1990). One amino acid change produces a high affinity cGMP-binding site in cAMP-dependent protein kinase. J. Biol. Chem. 265, 16031-16034.

Spraggon, G., Pantazatos, D., Klock, H. E., Wilson, I. A., Woods, V. L., Jr., and Lesley, S. A. (2004). On the use of DXMS to produce more crystallizable proteins: structures of the T. maritima proteins TM0160 and TM1171. Protein Sci. 13, 3187-3199.

Su, Y., Dostmann, W. R., Herberg, F. W., Durick, K., Xuong, N. H., Ten Eyck, L., Taylor, S. S., and Varughese, K. I. (1995). Regulatory subunit of protein kinase A: structure of deletion mutant with cAMP binding domains. Science 269, 807-813.

Takio, K., Wade, R. D., Smith, S. B., Krebs, E. G., Walsh, K. A., and Titani, K. (1984). Guanosine cyclic 30,50-phosphate dependent protein kinase, a chimeric protein homologous with two separate protein families Biochemistry 23, 4207-4218.

Tegge, W., Frank, R., Hofmann, F., and Dostmann, W. R. (1995). Determination of cyclic nucleotide-dependent protein kinase substrate specificity by the use of peptide libraries on cellulose paper. Biochemistry 34, 10569-10577.

Walter, U. and S. Gambaryan, *cGMP and cGMP-dependent protein kinase in platelets and blood cells.* Handbook of experimental pharmacology, 2009 (191): p. 533-48.

Weber, I. T., Shabb, J. B., and Corbin, J. D. (1989). Predicted structures of the cGMP binding domains of the cGMP-dependent protein kinase: a key alanine/threonine difference in evolutionary divergence of cAMP and cGMP binding sites. Biochemistry 28, 6122-6127.

Wu, J., Brown, S. H., von Daake, S., and Taylor, S. S. (2007). PKA type IIalpha holoenzyme reveals a combinatorial strategy for isoform diversity. Science 318, 274-279.

Zhang, Z., and Smith, D. L. (1993). Determination of amide hydrogen exchange by mass spectrometry: a new tool for protein structure elucidation. Protein Sci. 2, 522-531.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. An isolated synthetic peptide, wherein the peptide comprises $X_1X_2FFANLX_8$ (SEQ ID NO: 10), such that $X_1$ and $X_2$ are Ala, and $X_8$ is Lys, and wherein the peptide is 30 amino acids or less in length and wherein the peptide comprises a terminal modification.

2. The isolated synthetic peptide of claim 1, wherein the terminal modification is a C terminal modification with a blocking agent.

3. The isolated synthetic peptide of claim 2, wherein the blocking agent is an amide.

4. The isolated synthetic peptide of claim 1, wherein the terminal modification is a non-peptide moiety.

5. A composition comprising: the peptide of claim 1 and a carrier.

6. The composition of claim 5, wherein the peptide is: DVSNKAYEDAEAKAKYEAEAAFFANLKLSD (SEQ ID NO. 4).

* * * * *